US012565534B2

(12) United States Patent
Miao et al.

(10) Patent No.: US 12,565,534 B2
(45) Date of Patent: Mar. 3, 2026

(54) NANO-ANTIBODY TARGETING CAIX ANTIGEN AND APPLICATION THEREOF

(71) Applicant: BIOTHEUS INC., Zhuhai (CN)

(72) Inventors: Xiaoniu Miao, Guangdong (CN); Yifeng Xu, Guangdong (CN); Gang Yi, Guangdong (CN); Zhiyuan Li, Guangdong (CN); Andy Tsun, Guangdong (CN); Xiaolin Liu, Guangdong (CN)

(73) Assignee: BIOTHEUS INC., Guangdong (CN)

( * ) Notice: Subject to any disclaimer, the term of this patent is extended or adjusted under 35 U.S.C. 154(b) by 1030 days.

(21) Appl. No.: 17/641,801

(22) PCT Filed: Aug. 25, 2020

(86) PCT No.: PCT/CN2020/111112
§ 371 (c)(1),
(2) Date: Mar. 9, 2022

(87) PCT Pub. No.: WO2021/047386
PCT Pub. Date: Mar. 18, 2021

(65) Prior Publication Data
US 2023/0002503 A1 Jan. 5, 2023

(30) Foreign Application Priority Data
Sep. 10, 2019 (CN) .......................... 201910853699.9

(51) Int. Cl.
*A61K 47/68* (2017.01)
*A61K 39/00* (2006.01)
*C07K 16/30* (2006.01)

(52) U.S. Cl.
CPC .............. *C07K 16/30* (2013.01); *A61K 39/00* (2013.01); *A61K 47/6851* (2017.08); *C07K 2317/565* (2013.01); *C07K 2317/569* (2013.01); *C07K 2317/92* (2013.01)

(58) Field of Classification Search
CPC .............. C07K 16/30; C07K 2317/565; C07K 2317/569; C07K 2317/22; C07K 2317/24; C07K 2317/56; C07K 2317/567; A61K 39/00; A61K 47/6851; A61P 35/00; G01N 33/57484
See application file for complete search history.

(56) References Cited

U.S. PATENT DOCUMENTS

| | | | |
|---|---|---|---|
| 2009/0068095 A1 | 3/2009 | Marasco et al. |
| 2019/0276557 A1 | 9/2019 | Moon et al. |
| 2020/0289561 A1 | 9/2020 | Qian et al. |
| 2021/0221906 A1 | 7/2021 | Marasco |

FOREIGN PATENT DOCUMENTS

| | | |
|---|---|---|
| CN | 107523545 A | 12/2017 |
| CN | 108064251 A | 5/2018 |
| CN | 109705225 A | 5/2019 |
| CN | 109797171 A1 | 5/2019 |
| CN | 109996816 A | 7/2019 |
| WO | 2011/139375 A1 | 11/2011 |
| WO | 2016199097 A1 | 12/2016 |
| WO | 2018/157147 A1 | 8/2018 |

OTHER PUBLICATIONS

Goel et al. Plasticity within the Antigen-Combining Site May Manifest as Molecular Mimicry in the Humoral Immune Response. J Immunol (2004) 173 (12): 7358â7367. (Year: 2004).*

Lloyd et al.Modelling the human immune response: performance of a 1011 human antibody repertoire against a broad panel of therapeutically relevant antigens. Protein Engineering, Design & Selection vol. 22 No. 3 pp. 159â168, 2009. (Year: 2009).*

Rabia et al Understanding and overcoming trade-offs between antibody affinity, specificity, stability and solubility (Biochemical Engineering Journal 137 (2018) 365â374) (Year: 2018).*

Sabir et al. Construction of naive camelids VHH repertoire in phage display-based libraryC. R. Biologies 337 (2014) 244â249 (Year: 2014).*

International Search Report and Written Opinion dated Dec. 9, 2020, directed to International Application No. PCT/CN2020/111112; 7 pages.

Stravinskiene, D., (Jul. 2019). "New Monoclonal Antibodies for a Selective Detection of Membrane-Associated and Soluble Forms of Carbonic Anhydrase IX in Human Cell Lines and Biological Samples," in Biomolecules; 23 pages.

Wang, L. et al., (2017). "Study on Lung targeting of carbonic antibody IX modified norcantharidin nano-micelle," Pharmacology and Clinics of Chinese Materia Medica No. 1; pp. 52-56.

Li, J. et al., (Jul. 2012). "Radiolabeling of anti-carbonic anhydrase IX monoclonal antibody by 99Tcm and its imaging in the mouse bearing tumors" in Nuclear Techniques. vol. 35; No. 7; 4 pages.

(Continued)

*Primary Examiner* — Janet L Andres
*Assistant Examiner* — Brian Hartnett
(74) *Attorney, Agent, or Firm* — Michele V. Frank; Venable LLP

(57) ABSTRACT

Provided are an anti-CAIX single-domain antibody and a VHH chain thereof, as well as related coding sequence, expression vector and host cell; also provided are a production method for said CAIX single-domain antibody and an application thereof.

13 Claims, 2 Drawing Sheets
Specification includes a Sequence Listing.

(56)        References Cited

OTHER PUBLICATIONS

Ahlskog, JKJ. et al., (2009). "Human monoclonal antibodies targeting carbonic anhydrase IX for the molecular imaging of hypoxic regions in solid tumours," in British Journal of Cancer; pp. 645-657.

First Office Action dated Feb. 15, 2022, directed to Chinese Application No. CN201910853699.9; 14 pages.

First Office Action dated Mar. 1, 2024, directed to Chinese Application No. CN202080064128.8 14 pages.

F. Araste et al. "A novel VHH nanobody against the active site (the CA domain) of tumor-associated, carbonic anhydrase isoform IX and its usefulness for cancer diagnosis" Biotechnol Lett (2014) 36: pp. 21-28.

* cited by examiner

SEQUENCE LISTING

<160> NUMBER OF SEQ ID NOS: 93

<210> SEQ ID NO 1
<211> LENGTH: 8
<212> TYPE: PRT

```
<213> ORGANISM: Artificial sequence
<220> FEATURE:
<223> OTHER INFORMATION: H-YE-03 CDR1

<400> SEQUENCE: 1

Thr Ser Ser Phe Asn Phe Gln Thr
1               5

<210> SEQ ID NO 2
<211> LENGTH: 7
<212> TYPE: PRT
<213> ORGANISM: Artificial sequence
<220> FEATURE:
<223> OTHER INFORMATION: H-YE-03 CDR2

<400> SEQUENCE: 2

Ile Thr Ser Arg Ala Ile Thr
1               5

<210> SEQ ID NO 3
<211> LENGTH: 8
<212> TYPE: PRT
<213> ORGANISM: Artificial sequence
<220> FEATURE:
<223> OTHER INFORMATION: H-YE-03 CDR3

<400> SEQUENCE: 3

Asn Ala Ala Trp Ile Gly Asp Tyr
1               5

<210> SEQ ID NO 4
<211> LENGTH: 114
<212> TYPE: PRT
<213> ORGANISM: Artificial sequence
<220> FEATURE:
<223> OTHER INFORMATION: amino acid sequence of H-YE-03

<400> SEQUENCE: 4

Gln Val Gln Leu Gln Glu Ser Gly Gly Gly Leu Val Gln Pro Gly Gly
1               5                   10                  15

Ser Leu Arg Leu Ser Cys Thr Ala Ser Thr Ser Ser Phe Asn Phe Gln
            20                  25                  30

Thr Met Gly Trp Tyr Arg Gln Ala Pro Gly Lys Gln Arg Glu Leu Val
        35                  40                  45

Ala Thr Ile Thr Ser Arg Ala Ile Thr Asn Tyr Ala Asp Ser Val Lys
    50                  55                  60

Gly Arg Phe Thr Ile Ser Arg Asp Asn Ala Ala Lys Thr Val Ser Leu
65                  70                  75                  80

Gln Met Asn Ser Leu Lys Pro Glu Asp Thr Ala Val Tyr Tyr Cys Asn
                85                  90                  95

Ala Ala Trp Ile Gly Asp Tyr Trp Gly Gln Gly Thr Gln Val Thr Val
            100                 105                 110

Ser Ala

<210> SEQ ID NO 5
<211> LENGTH: 342
<212> TYPE: DNA
<213> ORGANISM: Artificial sequence
<220> FEATURE:
<223> OTHER INFORMATION: nucleotide sequence of H-YE-03

<400> SEQUENCE: 5
caggtgcagc tgcaggagtc tggggggaggc ttggtgcagc ctggggggtc tctgagactc    60
```

-continued

```
tcctgtacag cctctactag cagtttcaat ttccagacca tgggctggta ccgccaggct      120
ccagggaagc agcgcgagtt ggtcgcgaca attactagcc gtgctatcac aaactatgca      180
gactccgtga agggccgctt caccatctcc agagacaacg ccgcgaagac ggtgtctctg      240
caaatgaaca gccttaaacc tgaggacacg gccgtctatt actgtaatgc agcgtggatc      300
ggggactact ggggccaggg gacccaggtc accgtctccg ca                         342
```

```
<210> SEQ ID NO 6
<211> LENGTH: 8
<212> TYPE: PRT
<213> ORGANISM: Artificial sequence
<220> FEATURE:
<223> OTHER INFORMATION: H-YE-04 CDR1

<400> SEQUENCE: 6

Thr Ser Ser Phe Asn Phe Gln Thr
1               5

<210> SEQ ID NO 7
<211> LENGTH: 7
<212> TYPE: PRT
<213> ORGANISM: Artificial sequence
<220> FEATURE:
<223> OTHER INFORMATION: H-YE-04 CDR2

<400> SEQUENCE: 7

Ile Thr Ser Arg Ala Ile Thr
1               5

<210> SEQ ID NO 8
<211> LENGTH: 8
<212> TYPE: PRT
<213> ORGANISM: Artificial sequence
<220> FEATURE:
<223> OTHER INFORMATION: H-YE-04 CDR3

<400> SEQUENCE: 8

Asn Ala Ala Trp Ile Gly Asp Tyr
1               5

<210> SEQ ID NO 9
<211> LENGTH: 114
<212> TYPE: PRT
<213> ORGANISM: Artificial sequence
<220> FEATURE:
<223> OTHER INFORMATION: amino acid sequence of H-YE-04

<400> SEQUENCE: 9

Gln Val Gln Leu Gln Glu Ser Gly Gly Gly Leu Val Gln Pro Gly Gly
1               5                   10                  15

Ser Leu Arg Leu Ser Cys Thr Ala Ser Thr Ser Ser Phe Asn Phe Gln
            20                  25                  30

Thr Leu Gly Trp Tyr Arg Gln Ala Pro Gly Asn Gln Arg Glu Leu Val
        35                  40                  45

Ala Thr Ile Thr Ser Arg Ala Ile Thr Asn Tyr Ala Asp Ser Val Lys
    50                  55                  60

Gly Arg Phe Thr Ile Ser Arg Asp Asn Ala Ala Lys Thr Val Ser Leu
65                  70                  75                  80

Gln Met Asn Ser Leu Lys Pro Glu Asp Thr Ala Val Tyr Tyr Cys Asn
                85                  90                  95

Ala Ala Trp Ile Gly Asp Tyr Trp Gly Gln Gly Thr Gln Val Thr Val
```

-continued

```
          100             105             110

Ser Ser

<210> SEQ ID NO 10
<211> LENGTH: 342
<212> TYPE: DNA
<213> ORGANISM: Artificial sequence
<220> FEATURE:
<223> OTHER INFORMATION: nucleotide sequence of H-YE-04

<400> SEQUENCE: 10
caggtgcagc tgcaggagtc tggggggaggc ttggtgcagc ctggggggtc tctgagactc      60
tcctgtacag cctctactag cagtttcaat ttccagacct tgggctggta ccgccaggct     120
ccagggaatc agcgcgagtt ggtcgcgaca attactagcc gtgctatcac aaactatgca     180
gactccgtga agggccgctt caccatctcc agagacaacg ccgcgaagac ggtgtctctg     240
caaatgaaca gccttaaacc tgaggacacg gccgtctatt actgtaatgc agcgtggatc     300
ggggactact ggggccaggg gacccaggtc accgtctcca gt                        342

<210> SEQ ID NO 11
<211> LENGTH: 11
<212> TYPE: PRT
<213> ORGANISM: Artificial sequence
<220> FEATURE:
<223> OTHER INFORMATION: H-YE-05 CDR1

<400> SEQUENCE: 11

Gly Asn Ser Val Asn Ile Phe Ser Phe Ala Ala
1               5                   10

<210> SEQ ID NO 12
<211> LENGTH: 7
<212> TYPE: PRT
<213> ORGANISM: Artificial sequence
<220> FEATURE:
<223> OTHER INFORMATION: H-YE-05 CDR2

<400> SEQUENCE: 12

Ile Thr Thr Thr Gly Gly Thr
1               5

<210> SEQ ID NO 13
<211> LENGTH: 8
<212> TYPE: PRT
<213> ORGANISM: Artificial sequence
<220> FEATURE:
<223> OTHER INFORMATION: H-YE-05 CDR3

<400> SEQUENCE: 13

Asn Ala Asp Tyr Leu Gln Asp Tyr
1               5

<210> SEQ ID NO 14
<211> LENGTH: 117
<212> TYPE: PRT
<213> ORGANISM: Artificial sequence
<220> FEATURE:
<223> OTHER INFORMATION: amino acid sequence of H-YE-05

<400> SEQUENCE: 14

Gln Val Gln Leu Gln Glu Ser Gly Gly Gly Leu Val Gln Pro Gly Gly
1               5                   10                  15

Ser Arg Arg Leu Ser Cys Ala Ala Ser Gly Asn Ser Val Asn Ile Phe
```

-continued

```
                20            25            30

Ser Phe Ala Ala Val Ala Trp Tyr Arg Gln Ala Pro Gly Lys Gln Arg
        35            40            45

Glu Leu Val Ala Val Ile Thr Thr Thr Gly Gly Thr Lys Tyr Ser Asp
    50            55            60

Ser Val Lys Gly Arg Phe Thr Ile Ser Arg Asp Ser Ala Lys Asn Thr
65            70            75            80

Val Leu Leu Gln Met Asn Ser Leu Lys Pro Glu Asp Thr Ala Val Tyr
                85            90            95

Tyr Cys Asn Ala Asp Tyr Leu Gln Asp Tyr Trp Gly Gln Gly Thr Gln
            100           105           110

Val Thr Val Ser Ser
        115
```

```
<210> SEQ ID NO 15
<211> LENGTH: 351
<212> TYPE: DNA
<213> ORGANISM: Artificial sequence
<220> FEATURE:
<223> OTHER INFORMATION: nucleotide sequence of H-YE-05

<400> SEQUENCE: 15
caggtgcagc tgcaggagtc tggggggggc ttggtgcaac ctggggggtc tcgtcgactc      60
tcctgtgcag cctctggaaa ctctgtaaac atcttcagtt tcgctgccgt ggcctggtac     120
cgccaggctc cagggaagca gcgcgagttg gtcgcagtca ttactacgac aggtggcact     180
aagtattcag actccgtgaa gggccgattc accatctcca gagacagcgc caagaatacg     240
gtgcttctgc aaatgaacag cctgaaacct gaggacacgg ccgtctatta ctgtaatgca     300
gattatttac aggactactg gggccagggg acccaggtca ccgtctccag t             351
```

```
<210> SEQ ID NO 16
<211> LENGTH: 11
<212> TYPE: PRT
<213> ORGANISM: Artificial sequence
<220> FEATURE:
<223> OTHER INFORMATION: H-YE-23 CDR1

<400> SEQUENCE: 16

Gly Asn Ser Ala Asn Ile Phe Ser Phe Ala Ser
1               5                 10
```

```
<210> SEQ ID NO 17
<211> LENGTH: 7
<212> TYPE: PRT
<213> ORGANISM: Artificial sequence
<220> FEATURE:
<223> OTHER INFORMATION: H-YE-23 CDR2

<400> SEQUENCE: 17

Ile Thr Ser Ala Gly Gly Thr
1               5
```

```
<210> SEQ ID NO 18
<211> LENGTH: 8
<212> TYPE: PRT
<213> ORGANISM: Artificial sequence
<220> FEATURE:
<223> OTHER INFORMATION: H-YE-23 CDR3

<400> SEQUENCE: 18

Asn Val Asp Tyr Leu Gln Asp Tyr
```

1                    5

<210> SEQ ID NO 19
<211> LENGTH: 117
<212> TYPE: PRT
<213> ORGANISM: Artificial sequence
<220> FEATURE:
<223> OTHER INFORMATION: amino acid sequence of H-YE-23

<400> SEQUENCE: 19

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ser Ala Asn Ile Phe
            20                  25                  30

Ser Phe Ala Ser Val Ala Trp Tyr Arg Gln Ala Pro Gly Lys Gln Arg
        35                  40                  45

Glu Leu Val Ala Val Ile Thr Ser Ala Gly Gly Thr Lys Tyr Ser Asp
    50                  55                  60

Ser Val Lys Gly Arg Phe Thr Ile Ser Arg Asp Asn Ala Lys Asn Thr
65                  70                  75                  80

Ile Leu Leu Gln Met Asn Ser Leu Lys Pro Glu Asp Thr Ala Val Tyr
                85                  90                  95

Tyr Cys Asn Val Asp Tyr Leu Gln Asp Tyr Trp Gly Gln Gly Thr Gln
            100                 105                 110

Val Thr Val Ser Ser
        115

<210> SEQ ID NO 20
<211> LENGTH: 351
<212> TYPE: DNA
<213> ORGANISM: Artificial sequence
<220> FEATURE:
<223> OTHER INFORMATION: nucleotide sequence of H-YE-23

<400> SEQUENCE: 20
caggtgcagc tgcaggagtc tggaggaggc ttggtgcaac ctggggggtc tctaagactc      60
tcctgtgcag cctctggaaa ctctgctaac atcttcagtt tcgcgtccgt ggcctggtac     120
cgccaggctc agggaaaca gcgcgagttg gtcgcagtga tcactagtgc aggtggcact     180
aagtattcag actccgtgaa gggccgattc accatctcca gagacaacgc caagaatacg     240
attcttctgc aaatgaacag cctgaaacct gaggacacgg ccgtctatta ctgtaatgta     300
gattatttac aggactactg gggccagggg acccaggtca ccgtctccag t             351

<210> SEQ ID NO 21
<211> LENGTH: 11
<212> TYPE: PRT
<213> ORGANISM: Artificial sequence
<220> FEATURE:
<223> OTHER INFORMATION: H-YE-24 CDR1

<400> SEQUENCE: 21

Gly Asn Ser Val Asn Ile Phe Arg Phe Ala Ala
1               5                   10

<210> SEQ ID NO 22
<211> LENGTH: 7
<212> TYPE: PRT
<213> ORGANISM: Artificial sequence
<220> FEATURE:
<223> OTHER INFORMATION: H-YE-24 CDR2

```
<400> SEQUENCE: 22

Ile Thr Ser Ala Gly Gly Thr
1               5

<210> SEQ ID NO 23
<211> LENGTH: 8
<212> TYPE: PRT
<213> ORGANISM: Artificial sequence
<220> FEATURE:
<223> OTHER INFORMATION: H-YE-24 CDR3

<400> SEQUENCE: 23

Asn Ala Asp Tyr Leu Gln Asp Tyr
1               5

<210> SEQ ID NO 24
<211> LENGTH: 117
<212> TYPE: PRT
<213> ORGANISM: Artificial sequence
<220> FEATURE:
<223> OTHER INFORMATION: amino acid sequence of H-YE-24

<400> SEQUENCE: 24

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ser Val Asn Ile Phe
            20                  25                  30

Arg Phe Ala Ala Met Ala Trp Tyr Arg Gln Ala Pro Gly Lys Gln Arg
        35                  40                  45

Glu Leu Val Ala Val Ile Thr Ser Ala Gly Gly Thr Lys Tyr Ser Asp
    50                  55                  60

Ser Val Lys Gly Arg Phe Thr Ile Ser Arg Asp Asn Ala Lys Asn Thr
65                  70                  75                  80

Val Leu Leu Gln Met Asn Ser Leu Lys Pro Glu Asp Thr Ala Val Tyr
                85                  90                  95

Tyr Cys Asn Ala Asp Tyr Leu Gln Asp Tyr Trp Gly Gln Gly Thr Gln
            100                 105                 110

Val Thr Val Ser Ser
        115

<210> SEQ ID NO 25
<211> LENGTH: 351
<212> TYPE: DNA
<213> ORGANISM: Artificial sequence
<220> FEATURE:
<223> OTHER INFORMATION: nucleotide sequence of H-YE-24

<400> SEQUENCE: 25
caggtgcagc tgcaggagtc tgggggaggc ttggtgcagc ctggggggtc tctaagactc      60
tcctgtgcag cctctggaaa ctctgtaaac atcttcagat tcgctgccat ggcctggtac     120
cgccaggctc cagggaagca gcgcgagttg gtcgcagtca ttactagtgc aggtggcact     180
aagtattcag actccgtgaa gggccgattc accatctcca gagacaacgc caagaatacg     240
gtgcttctgc aaatgaacag cctgaaacct gaggacacgg ccgtctatta ctgtaatgca     300
gattatttac aggactactg gggccagggg acccaggtca ccgtctccag t              351

<210> SEQ ID NO 26
<211> LENGTH: 11
<212> TYPE: PRT
<213> ORGANISM: Artificial sequence
```

```
<220> FEATURE:
<223> OTHER INFORMATION: H-YE-25 CDR1

<400> SEQUENCE: 26

Gly Asn Ser Val Asn Ile Phe Arg Phe Ala Ala
1               5                   10

<210> SEQ ID NO 27
<211> LENGTH: 7
<212> TYPE: PRT
<213> ORGANISM: Artificial sequence
<220> FEATURE:
<223> OTHER INFORMATION: H-YE-25 CDR2

<400> SEQUENCE: 27

Ile Thr Thr Thr Gly Gly Thr
1               5

<210> SEQ ID NO 28
<211> LENGTH: 8
<212> TYPE: PRT
<213> ORGANISM: Artificial sequence
<220> FEATURE:
<223> OTHER INFORMATION: H-YE-25 CDR3

<400> SEQUENCE: 28

Asn Ala Asp Tyr Leu Gln Asp Tyr
1               5

<210> SEQ ID NO 29
<211> LENGTH: 117
<212> TYPE: PRT
<213> ORGANISM: Artificial sequence
<220> FEATURE:
<223> OTHER INFORMATION: amino acid sequence of H-YE-25

<400> SEQUENCE: 29

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ser Val Asn Ile Phe
            20                  25                  30

Arg Phe Ala Ala Met Ala Trp Tyr Arg Gln Ala Pro Gly Lys Gln Arg
        35                  40                  45

Glu Leu Val Ala Val Ile Thr Thr Thr Gly Gly Thr Lys Tyr Ser Asp
    50                  55                  60

Ser Val Lys Gly Arg Phe Thr Ile Ser Arg Asp Ser Ala Lys Asn Thr
65                  70                  75                  80

Val Leu Leu Gln Met Asn Ser Leu Lys Pro Glu Asp Thr Ala Val Tyr
                85                  90                  95

Tyr Cys Asn Ala Asp Tyr Leu Gln Asp Tyr Trp Gly Gln Gly Thr Gln
            100                 105                 110

Val Thr Val Ser Ser
        115

<210> SEQ ID NO 30
<211> LENGTH: 351
<212> TYPE: DNA
<213> ORGANISM: Artificial sequence
<220> FEATURE:
<223> OTHER INFORMATION: nucleotide sequence of H-YE-25

<400> SEQUENCE: 30
caggtgcagc tgcaggagtc tggaggaggc ttggtgcaac ctggggggtc tctaagactc      60
```

```
tcctgtgcag cctctggaaa ctctgtaaac atcttcagat tcgctgccat ggcctggtac      120
cgccaggctc cagggaagca gcgcgagttg gtcgcagtca ttactacgac aggtggcact      180
aagtattcag actccgtgaa gggccgattc accatctcca gagacagcgc caagaatacg      240
gtgcttctgc aaatgaacag cctgaaacct gaggacacgg ccgtctatta ctgtaatgca      300
gattatttac aggactactg gggccagggg acccaggtca ccgtctccag t              351
```

```
<210> SEQ ID NO 31
<211> LENGTH: 11
<212> TYPE: PRT
<213> ORGANISM: Artificial sequence
<220> FEATURE:
<223> OTHER INFORMATION: H-YE-26 CDR1

<400> SEQUENCE: 31

Gly Asn Ser Val Asn Ile Phe Arg Phe Ala Thr
1               5                   10

<210> SEQ ID NO 32
<211> LENGTH: 7
<212> TYPE: PRT
<213> ORGANISM: Artificial sequence
<220> FEATURE:
<223> OTHER INFORMATION: H-YE-26 CDR2

<400> SEQUENCE: 32

Ile Thr Ser Ala Gly Gly Thr
1               5

<210> SEQ ID NO 33
<211> LENGTH: 8
<212> TYPE: PRT
<213> ORGANISM: Artificial sequence
<220> FEATURE:
<223> OTHER INFORMATION: H-YE-26 CDR3

<400> SEQUENCE: 33

Asn Ala Asp Phe Leu Gln Asp Tyr
1               5

<210> SEQ ID NO 34
<211> LENGTH: 117
<212> TYPE: PRT
<213> ORGANISM: Artificial sequence
<220> FEATURE:
<223> OTHER INFORMATION: amino acid sequence of H-YE-26

<400> SEQUENCE: 34

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ser Val Asn Ile Phe
            20                  25                  30

Arg Phe Ala Thr Val Ala Trp Tyr Arg Gln Ala Pro Gly Glu Gln Arg
        35                  40                  45

Glu Leu Val Ala Val Ile Thr Ser Ala Gly Gly Thr Lys Tyr Ser Asp
    50                  55                  60

Ser Val Lys Gly Arg Phe Thr Ile Ser Arg Asp Asn Ala Lys Asn Thr
65                  70                  75                  80

Val Leu Leu Gln Met Asn Ser Leu Lys Pro Glu Asp Thr Ala Val Tyr
                85                  90                  95

Tyr Cys Asn Ala Asp Phe Leu Gln Asp Tyr Trp Gly Gln Gly Thr Gln
```

-continued

```
              100              105              110

Val Thr Val Ser Ser
        115

<210> SEQ ID NO 35
<211> LENGTH: 351
<212> TYPE: DNA
<213> ORGANISM: Artificial sequence
<220> FEATURE:
<223> OTHER INFORMATION: nucleotide sequence of H-YE-26

<400> SEQUENCE: 35
caggtgcagc tgcaggagtc tgggggaggc ttggtgcagg ctgggggtc tctgagactc          60 tcctgtgcag cctctggaaa ctctgtgaac atcttcaggt tcgctaccgt agcctggtac         120
cgccaggctc caggggagca gcgcgagttg gtcgcagtca ttactagtgc aggtggcact         180
aagtattcag actccgtgaa gggccgattc accatctcca gagacaacgc caagaatacg         240
gtgcttctgc aaatgaacag cctgaaacct gaggacacgg ccgtctatta ttgtaatgca         300
gattttttac aggactactg gggccagggg acccaggtca ccgtctccag t                  351

<210> SEQ ID NO 36
<211> LENGTH: 11
<212> TYPE: PRT
<213> ORGANISM: Artificial sequence
<220> FEATURE:
<223> OTHER INFORMATION: H-YE-32 CDR1

<400> SEQUENCE: 36

Gly Gly Ala Arg Asn Ile Phe Ser Phe Ala Ala
1               5                   10

<210> SEQ ID NO 37
<211> LENGTH: 7
<212> TYPE: PRT
<213> ORGANISM: Artificial sequence
<220> FEATURE:
<223> OTHER INFORMATION: H-YE-32 CDR2

<400> SEQUENCE: 37

Ile Thr Ser Ala Gly Gly Thr
1               5

<210> SEQ ID NO 38
<211> LENGTH: 8
<212> TYPE: PRT
<213> ORGANISM: Artificial sequence
<220> FEATURE:
<223> OTHER INFORMATION: H-YE-32 CDR3

<400> SEQUENCE: 38

Asn Ala Asp Tyr Tyr Gln Asp Tyr
1               5

<210> SEQ ID NO 39
<211> LENGTH: 117
<212> TYPE: PRT
<213> ORGANISM: Artificial sequence
<220> FEATURE:
<223> OTHER INFORMATION: amino acid sequence of H-YE-32

<400> SEQUENCE: 39

Gln Val Gln Leu Gln Glu Ser Gly Gly Gly Leu Val Gln Pro Gly Gly
1               5                   10                  15
```

-continued

```
Ser Leu Arg Leu Ser Cys Ala Ala Ser Gly Gly Ala Arg Asn Ile Phe
            20                  25                  30

Ser Phe Ala Ala Met Ala Trp Tyr Arg Gln Ala Pro Gly Lys Gln Arg
        35                  40                  45

Glu Leu Val Ala Val Ile Thr Ser Ala Gly Gly Thr Gln Tyr Ser Ser
    50                  55                  60

Ser Val Lys Gly Arg Phe Thr Ile Ser Arg Asp Asn Ala Lys Lys Thr
65                  70                  75                  80

Val Leu Leu Gln Met Asn Ser Leu Lys Pro Glu Asp Thr Ala Val Tyr
                85                  90                  95

Tyr Cys Asn Ala Asp Tyr Tyr Gln Asp Tyr Trp Gly Gln Gly Thr Gln
            100                 105                 110

Val Thr Val Ser Ser
        115
```

```
<210> SEQ ID NO 40
<211> LENGTH: 351
<212> TYPE: DNA
<213> ORGANISM: Artificial sequence
<220> FEATURE:
<223> OTHER INFORMATION: nucleotide sequence of H-YE-32

<400> SEQUENCE: 40
caggtgcagc tgcaggagtc tgggggaggc ttggtgcaac ctggggggtc tctaagactc      60
tcctgtgcag cctctggagg cgctagaaac atcttcagct tcgctgccat ggcctggtac     120
cgccaggctc cagggaagca gcgcgagttg gtcgcagtca ttactagtgc aggaggcacg     180
cagtattcaa gctccgtgaa gggccgattc accatctcca gagacaacgc caagaaaacg     240
gtattgctgc aaatgaacag cctgaaacct gaggacacgg ccgtctatta ctgtaatgca     300
gattattatc aggactactg gggccagggg acccaggtca ccgtctccag t              351
```

```
<210> SEQ ID NO 41
<211> LENGTH: 8
<212> TYPE: PRT
<213> ORGANISM: Artificial sequence
<220> FEATURE:
<223> OTHER INFORMATION: H-YE-33 CDR1

<400> SEQUENCE: 41

Gly Gly Asp Phe Arg Phe Tyr Asp
1               5
```

```
<210> SEQ ID NO 42
<211> LENGTH: 7
<212> TYPE: PRT
<213> ORGANISM: Artificial sequence
<220> FEATURE:
<223> OTHER INFORMATION: H-YE-33 CDR2

<400> SEQUENCE: 42

Ile Thr Thr Arg Gly Tyr Thr
1               5
```

```
<210> SEQ ID NO 43
<211> LENGTH: 12
<212> TYPE: PRT
<213> ORGANISM: Artificial sequence
<220> FEATURE:
<223> OTHER INFORMATION: H-YE-33 CDR3

<400> SEQUENCE: 43
```

-continued

```
Ser Ala Ser His Phe Leu Gly Gly Arg Ile Asp Tyr
1               5                   10

<210> SEQ ID NO 44
<211> LENGTH: 118
<212> TYPE: PRT
<213> ORGANISM: Artificial sequence
<220> FEATURE:
<223> OTHER INFORMATION: amino acid sequence of H-YE-33

<400> SEQUENCE: 44

Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Asp Phe Arg Phe Tyr
            20                  25                  30

Asp Met Gly Trp Tyr Arg Gln Ala Pro Gly Lys Gln Arg Glu Leu Val
        35                  40                  45

Ala Gly Ile Thr Thr Arg Gly Tyr Thr Asn Tyr Ala Asp Val Val Lys
    50                  55                  60

Gly Arg Phe Thr Ile Ser Arg Asp Asn Ala Lys Asn Thr Val Tyr Leu
65                  70                  75                  80

Glu Met Asn Ser Leu Lys Pro Glu Asp Thr Ala Val Tyr Ser Cys Ser
                85                  90                  95

Ala Ser His Phe Leu Gly Gly Arg Ile Asp Tyr Trp Gly Gln Gly Thr
            100                 105                 110

Gln Val Thr Val Ser Ser
        115

<210> SEQ ID NO 45
<211> LENGTH: 354
<212> TYPE: DNA
<213> ORGANISM: Artificial sequence
<220> FEATURE:
<223> OTHER INFORMATION: nucleotide sequence  of H-YE-33

<400> SEQUENCE: 45
caggtgcagc tgcaggagtc tggaggaggc ttggtgcagc ctggggggtc tctgagactc      60
tcctgtgcag cctctggagg ggacttcagg ttctatgaca tgggctggta ccgccaggct     120
ccagggaagc agcgcgagtt ggtcgcaggt attactactc gtggctacac caactatgca     180
gacgtcgtga agggccgatt caccatctcc agagacaacg ccaagaacac ggtgtatctg     240
gaaatgaaca gcctgaaacc tgaggacacg gccgtctatt cctgtagtgc aagtcacttc     300
ctgggcggga aatagacta ctggggccag gggacccagg tcaccgtctc cagt            354

<210> SEQ ID NO 46
<211> LENGTH: 8
<212> TYPE: PRT
<213> ORGANISM: Artificial sequence
<220> FEATURE:
<223> OTHER INFORMATION: H-YE-37 CDR1

<400> SEQUENCE: 46

Gly Arg Thr Phe Ser Thr Tyr Ala
1               5

<210> SEQ ID NO 47
<211> LENGTH: 8
<212> TYPE: PRT
<213> ORGANISM: Artificial sequence
<220> FEATURE:
<223> OTHER INFORMATION: H-YE-37 CDR2
```

<400> SEQUENCE: 47

Ile Ser Trp Ser Gly Gly Ser Thr
1               5

<210> SEQ ID NO 48
<211> LENGTH: 20
<212> TYPE: PRT
<213> ORGANISM: Artificial sequence
<220> FEATURE:
<223> OTHER INFORMATION: H-YE-37 CDR3

<400> SEQUENCE: 48

Ala Ala Glu Gly Ile Tyr Asn Ser Gly Ser Ser Tyr His Asp Ala Asn
1               5                   10                  15

Gly Tyr Asp Tyr
            20

<210> SEQ ID NO 49
<211> LENGTH: 127
<212> TYPE: PRT
<213> ORGANISM: Artificial sequence
<220> FEATURE:
<223> OTHER INFORMATION: amino acid sequence of H-YE-37

<400> SEQUENCE: 49

Gln Val Gln Leu Gln Glu Ser Gly Gly Gly Leu Met His Asp Gly Asp
1               5                   10                  15

Ser Leu Arg Leu Ser Cys Ala Ala Ser Gly Arg Thr Phe Ser Thr Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Gly Ile Tyr Asn Ser Gly Ser Ser Tyr His Asp Ala Asn
            100                 105                 110

Gly Tyr Asp Tyr Trp Gly Gln Gly Thr Gln Val Thr Val Ser Ser
        115                 120                 125

<210> SEQ ID NO 50
<211> LENGTH: 381
<212> TYPE: DNA
<213> ORGANISM: Artificial sequence
<220> FEATURE:
<223> OTHER INFORMATION: nucleotide sequence of H-YE-37

<400> SEQUENCE: 50
caggtgcagc tgcaggagtc tggaggagga ttgatgcatg atggggactc tctgagactc        60
tcctgtgcag cctctggacg caccttcagt acctatgcca tgggctggtt ccgccaggct       120
ccagggaagg agcgtgagtt tgtagcagct attagctgga gtggtggtag cacatactat       180
gcagactccg tgaagggccg attcaccatc tccagagaca cgccaagaa cacggtgtat        240 ctgcaaatga acagcctgaa acctgaggac acggccgttt attactgtgc agcagagggg       300
atatacaata gtggtagttc gtaccatgac gcgaacgggt atgactactg gggccagggg       360
acccaggtca ccgtctccag t                                                  381

```
<210> SEQ ID NO 51
<211> LENGTH: 8
<212> TYPE: PRT
<213> ORGANISM: Artificial sequence
<220> FEATURE:
<223> OTHER INFORMATION: H-YE-38 CDR1

<400> SEQUENCE: 51

Arg Phe Thr Leu Asp Tyr Tyr Ala
1               5

<210> SEQ ID NO 52
<211> LENGTH: 8
<212> TYPE: PRT
<213> ORGANISM: Artificial sequence
<220> FEATURE:
<223> OTHER INFORMATION: H-YE-38 CDR2

<400> SEQUENCE: 52

Ile Ser Trp Ser Gly Gly Thr Thr
1               5

<210> SEQ ID NO 53
<211> LENGTH: 13
<212> TYPE: PRT
<213> ORGANISM: Artificial sequence
<220> FEATURE:
<223> OTHER INFORMATION: H-YE-38 CDR3

<400> SEQUENCE: 53

Ala Ala Gly Arg Gln Leu Glu Trp Arg Thr Tyr Asp Tyr
1               5                   10

<210> SEQ ID NO 54
<211> LENGTH: 120
<212> TYPE: PRT
<213> ORGANISM: Artificial sequence
<220> FEATURE:
<223> OTHER INFORMATION: amino acid sequence of H-YE-38

<400> SEQUENCE: 54

Gln Val Gln Leu Gln Glu Ser Gly Gly Gly Leu Met Gln Pro Gly Gly
1               5                   10                  15

Ser Leu Thr Leu Ser Cys Ala Val Pro Arg Phe Thr Leu Asp Tyr Tyr
            20                  25                  30

Ala Ile Gly Trp Phe Arg Gln Ala Pro Gly Lys Glu Arg Glu Phe Val
        35                  40                  45

Ala Ala Ile Ser Trp Ser Gly Gly Thr Thr Gln Tyr Ser Asp Ser Ala
    50                  55                  60

Lys Gly Arg Phe Thr Ile Ser Arg Asp Asn Ser Lys Asn Thr Gly Tyr
65                  70                  75                  80

Leu Gln Met Asn Ser Leu Lys Pro Glu Asp Thr Ala Thr Tyr Tyr Cys
                85                  90                  95

Ala Ala Gly Arg Gln Leu Glu Trp Arg Thr Tyr Asp Tyr Trp Gly Gln
            100                 105                 110

Gly Thr Gln Val Thr Val Ser Ser
        115                 120

<210> SEQ ID NO 55
<211> LENGTH: 360
<212> TYPE: DNA
<213> ORGANISM: Artificial sequence
```

-continued

<220> FEATURE:
<223> OTHER INFORMATION: nucleotide sequence of H-YE-38

<400> SEQUENCE: 55
caggtgcagc tgcaggagtc tggggggaggc ttgatgcagc ctggggggtc tctgacgctc        60
tcctgtgcag tccctagatt cactttggat tattatgcca taggctggtt ccggcaggcc       120
ccagggaagg agcgtgaatt tgtagcagct attagctgga gtggtggtac aacacagtat       180
tcagactccg cgaagggccg attcaccatc tccagagaca acagcaagaa tacggggtat       240
ctgcaaatga acagcctgaa acctgaggac acggcgactt attactgtgc agcaggtcgc       300
caactggagt ggaggacgta tgactactgg ggccagggga cccaggtcac cgtctccagt       360

<210> SEQ ID NO 56
<211> LENGTH: 8
<212> TYPE: PRT
<213> ORGANISM: Artificial sequence
<220> FEATURE:
<223> OTHER INFORMATION: H-YE-40 CDR1

<400> SEQUENCE: 56

Gly Arg Thr Phe Ser Ser Tyr Ala
1               5

<210> SEQ ID NO 57
<211> LENGTH: 8
<212> TYPE: PRT
<213> ORGANISM: Artificial sequence
<220> FEATURE:
<223> OTHER INFORMATION: H-YE-40 CDR2

<400> SEQUENCE: 57

Ile Ser Trp Asn Gly Gly Ser Thr
1               5

<210> SEQ ID NO 58
<211> LENGTH: 16
<212> TYPE: PRT
<213> ORGANISM: Artificial sequence
<220> FEATURE:
<223> OTHER INFORMATION: H-YE-40 CDR3

<400> SEQUENCE: 58

Ala Ala Glu His Asp Leu Gly Glu Leu Ala Gly Thr Gly Tyr Asp Tyr
1               5                   10                  15

<210> SEQ ID NO 59
<211> LENGTH: 123
<212> TYPE: PRT
<213> ORGANISM: Artificial sequence
<220> FEATURE:
<223> OTHER INFORMATION: amino acid sequence of H-YE-40

<400> SEQUENCE: 59

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Thr Ile Ser Trp Asn Gly Gly Ser Thr Tyr Tyr Ala Asp Ser Val
        50                  55                  60

Lys Gly Arg Phe Thr Ile Ser Arg Asp Asn Ala Lys Asn Thr Val Tyr

```
                65                  70                  75                  80
Leu Gln Met Asn Ser Leu Lys Pro Glu Asp Thr Ala Val Tyr Tyr Cys
                        85                  90                  95

Ala Ala Glu His Asp Leu Gly Glu Leu Ala Gly Thr Gly Tyr Asp Tyr
                100                 105                 110

Trp Gly Gln Gly Thr Gln Val Thr Val Ser Ser
        115                 120
```

```
<210> SEQ ID NO 60
<211> LENGTH: 369
<212> TYPE: DNA
<213> ORGANISM: Artificial sequence
<220> FEATURE:
<223> OTHER INFORMATION: nucleotide sequence of H-YE-40

<400> SEQUENCE: 60
caggtgcagc tgcaggagtc tggaggagga ttggtgcagg ctggggggctc tctgagactc        60 tcctgtgcag cctctggacg caccttcagt agctatgcca tgggctggtt ccgccaggct       120
ccagggaagg agcgtgagtt tgtagcaact attagctgga atggtggtag cacatactat       180
gcagactccg tgaagggccg attcaccatc tccagagaca cgccaagaa cacggtgtat        240 ctgcaaatga acagcctgaa acctgaggac acggccgttt attactgtgc agcagaacat       300
gatttggggg agctggcggg aactggttat gactactggg gccagggggac ccaggtcacc       360 gtctccagt                                                                369
```

```
<210> SEQ ID NO 61
<211> LENGTH: 117
<212> TYPE: PRT
<213> ORGANISM: Artificial sequence
<220> FEATURE:
<223> OTHER INFORMATION: amino acid sequence of Hu-H-YE-05-D3

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Asn Ser Val Asn Ile Phe
                20                  25                  30

Ser Phe Ala Ala Met Ser Trp Tyr Arg Gln Ala Pro Gly Lys Gly Leu
        35                  40                  45

Glu Leu Val Ala Val Ile Thr Thr Thr Gly Gly Thr Lys Tyr Ser Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Asn Ala Asp Tyr Leu Gln Asp Tyr Trp Gly Gln Gly Thr Gln
            100                 105                 110

Val Thr Val Ser Ser
        115
```

```
<210> SEQ ID NO 62
<211> LENGTH: 351
<212> TYPE: DNA
<213> ORGANISM: Artificial sequence
<220> FEATURE:
<223> OTHER INFORMATION: nucleotide sequence of Hu-H-YE-05-D3

<400> SEQUENCE: 62
```

-continued

```
gaggtgcagc tgctggagag cggcggcggc ctggtgcagc ccggcggcag cctgaggctg        60
agctgcgccg ccagcggcaa cagcgtgaac atcttcagct tcgccgccat gagctggtac       120
aggcaggccc ccggcaaggg cctggagctg gtggccgtga tcaccaccac cggcggcacc       180
aagtacagcg acagcgtgaa gggcaggttc accatcagca gggacaacag caagaacacc       240
ctgtacctgc agatgaacag cctgagggcc gaggacaccg ccgtgtacta ctgcaacgcc       300
gactacctgc aggactactg gggccagggc acccaggtga ccgtgagcag c                351
```

<210> SEQ ID NO 63
<211> LENGTH: 117
<212> TYPE: PRT
<213> ORGANISM: Artificial sequence
<220> FEATURE:
<223> OTHER INFORMATION: amino acid sequence of Hu-H-YE-05-D4

<400> SEQUENCE: 63

```
Glu Val Gln Leu Leu Glu Ser Gly Gly Gly Leu Val Gln Pro Gly Gly
1               5                   10                  15

Ser Arg Arg Leu Ser Cys Ala Ala Ser Gly Asn Ser Val Asn Ile Phe
            20                  25                  30

Ser Phe Ala Ala Val Ala Trp Tyr Arg Gln Ala Pro Gly Lys Gln Arg
        35                  40                  45

Glu Leu Val Ala Val Ile Thr Thr Thr Gly Gly Thr Lys Tyr Ser Asp
    50                  55                  60

Ser Val Lys Gly Arg Phe Thr Ile Ser Arg Asp Ser Ser Lys Asn Thr
65                  70                  75                  80

Val Tyr Leu Gln Met Asn Ser Leu Arg Ala Glu Asp Thr Ala Val Tyr
                85                  90                  95

Tyr Cys Asn Ala Asp Tyr Leu Gln Asp Tyr Trp Gly Gln Gly Thr Gln
            100                 105                 110

Val Thr Val Ser Ser
        115
```

<210> SEQ ID NO 64
<211> LENGTH: 351
<212> TYPE: DNA
<213> ORGANISM: Artificial sequence
<220> FEATURE:
<223> OTHER INFORMATION: nucleotide sequence of Hu-H-YE-05-D4

<400> SEQUENCE: 64

```
gaggtgcagc tgctggagag cggcggcggc ctggtgcagc ccggcggcag caggaggctg        60
agctgcgccg ccagcggcaa cagcgtgaac atcttcagct tcgccgccgt ggcctggtac       120
aggcaggccc ccggcaagca gagggagctg gtggccgtga tcaccaccac cggcggcacc       180
aagtacagcg acagcgtgaa gggcaggttc accatcagca gggacagcag caagaacacc       240
gtgtacctgc agatgaacag cctgagggcc gaggacaccg ccgtgtacta ctgcaacgcc       300
gactacctgc aggactactg gggccagggc acccaggtga ccgtgagcag c                351
```

<210> SEQ ID NO 65
<211> LENGTH: 117
<212> TYPE: PRT
<213> ORGANISM: Artificial sequence
<220> FEATURE:
<223> OTHER INFORMATION: amino acid sequence of Hu-H-YE-23-D2

<400> SEQUENCE: 65

```
Gln Val Gln Leu Val Glu Ser Gly Gly Gly Leu Val Gln Pro Gly Gly
```

```
1               5               10              15

Ser Leu Arg Leu Ser Cys Ser Ala Ser Gly Asn Ser Ala Asn Ile Phe
            20              25              30

Ser Phe Ala Ser Val Ala Trp Tyr Arg Gln Ala Pro Gly Lys Gly Leu
        35              40              45

Glu Leu Val Ser Val Ile Thr Ser Ala Gly Gly Thr Lys Tyr Ser Asp
    50              55              60

Ser Val Lys Gly Arg Phe Thr Ile Ser Arg Asp Asn Ser Lys Asn Thr
65              70              75              80

Leu Tyr Leu Gln Met Asn Ser Leu Arg Ala Glu Asp Thr Ala Val Tyr
            85              90              95

Tyr Cys Asn Val Asp Tyr Leu Gln Asp Tyr Trp Gly Gln Gly Thr Leu
        100             105             110

Val Thr Val Ser Ser
        115

<210> SEQ ID NO 66
<211> LENGTH: 351
<212> TYPE: DNA
<213> ORGANISM: Artificial sequence
<220> FEATURE:
<223> OTHER INFORMATION: nucleotide sequence of Hu-H-YE-23-D2

<400> SEQUENCE: 66
caggtgcagc tggtggagag cggcggcggc ctggtgcagc ccggcggcag cctgaggctg      60
agctgcagcg ccagcggcaa cagcgccaac atcttcagct tcgccagcgt ggcctggtac     120
aggcaggccc ccggcaaggg cctggagctg gtgagcgtga tcaccagcgc cggcggcacc     180
aagtacagcg acagcgtgaa gggcaggttc accatcagca gggacaacag caagaacacc     240
ctgtacctgc agatgaacag cctgagggcc gaggacaccg ccgtgtacta ctgcaacgtg     300
gactacctgc aggactactg gggccagggc accctggtga ccgtgagcag c              351

<210> SEQ ID NO 67
<211> LENGTH: 117
<212> TYPE: PRT
<213> ORGANISM: Artificial sequence
<220> FEATURE:
<223> OTHER INFORMATION: amino acid sequence of Hu-H-YE-32-D6

<400> SEQUENCE: 67

Gln Val Gln Leu Val Glu Ser Gly Gly Gly Leu Val Gln Pro Gly Gly
1               5               10              15

Ser Leu Arg Leu Ser Cys Ser Ala Ser Gly Gly Ala Arg Asn Ile Phe
            20              25              30

Ser Phe Ala Ala Met Ala Trp Tyr Arg Gln Ala Pro Gly Lys Gly Leu
        35              40              45

Glu Leu Val Ala Val Ile Thr Ser Ala Gly Gly Thr Gln Tyr Ser Ser
    50              55              60

Ser Val Lys Gly Arg Phe Thr Ile Ser Arg Asp Asn Ser Lys Lys Thr
65              70              75              80

Leu Tyr Leu Gln Met Asn Ser Leu Arg Ala Glu Asp Thr Ala Val Tyr
            85              90              95

Tyr Cys Asn Ala Asp Tyr Tyr Gln Asp Tyr Trp Gly Gln Gly Thr Gln
        100             105             110

Val Thr Val Ser Ser
        115
```

-continued

```
<210> SEQ ID NO 68
<211> LENGTH: 351
<212> TYPE: DNA
<213> ORGANISM: Artificial sequence
<220> FEATURE:
<223> OTHER INFORMATION: nucleotide sequence of Hu-H-YE-32-D6

<400> SEQUENCE: 68
caggtgcagc tggtggagag cggcggcggc ctggtgcagc ccggcggcag cctgaggctg       60
agctgcagcg ccagcggcgg cgccaggaac atcttcagct tcgccgccat ggcctggtac      120
aggcaggccc ccggcaaggg cctggagctg gtggccgtga tcaccagcgc cggcggcacc      180
cagtacagca gcagcgtgaa gggcaggttc accatcagca gggacaacag caagaagacc      240
ctgtacctgc agatgaacag cctgagggcc gaggacaccg ccgtgtacta ctgcaacgcc      300
gactactacc aggactactg gggccagggc acccaggtga ccgtgagcag c               351

<210> SEQ ID NO 69
<211> LENGTH: 117
<212> TYPE: PRT
<213> ORGANISM: Artificial sequence
<220> FEATURE:
<223> OTHER INFORMATION: amino acid sequence of Hu-H-YE-32-D5

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ser Ala Ser Gly Gly Ala Arg Asn Ile Phe
            20                  25                  30

Ser Phe Ala Ala Met His Trp Tyr Arg Gln Ala Pro Gly Lys Gly Leu
        35                  40                  45

Glu Leu Val Ala Val Ile Thr Ser Ala Gly Gly Thr Tyr Tyr Ala Asp
    50                  55                  60

Ser Val Lys Gly Arg Phe Thr Ile Ser Arg Asp Asn Ser Lys Lys Thr
65                  70                  75                  80

Leu Tyr Leu Gln Met Asn Ser Leu Arg Ala Glu Asp Thr Ala Val Tyr
                85                  90                  95

Tyr Cys Asn Ala Asp Tyr Tyr Gln Asp Tyr Trp Gly Gln Gly Thr Gln
            100                 105                 110

Val Thr Val Ser Ser
        115

<210> SEQ ID NO 70
<211> LENGTH: 351
<212> TYPE: DNA
<213> ORGANISM: Artificial sequence
<220> FEATURE:
<223> OTHER INFORMATION: nucleotide sequence of Hu-H-YE-32-D5

<400> SEQUENCE: 70
caggtgcagc tggtggagag cggcggcggc ctggtgcagc ccggcggcag cctgaggctg       60
agctgcagcg ccagcggcgg cgccaggaac atcttcagct tcgccgccat gcactggtac      120
aggcaggccc ccggcaaggg cctggagctg gtggccgtga tcaccagcgc cggcggcacc      180
tactacgccg acagcgtgaa gggcaggttc accatcagca gggacaacag caagaagacc      240
ctgtacctgc agatgaacag cctgagggcc gaggacaccg ccgtgtacta ctgcaacgcc      300
gactactacc aggactactg gggccagggc acccaggtga ccgtgagcag c               351
```

-continued

```
<210> SEQ ID NO 71
<211> LENGTH: 25
<212> TYPE: PRT
<213> ORGANISM: Artificial sequence
<220> FEATURE:
<223> OTHER INFORMATION: Hu-H-YE-05-D3 FR1

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 72
<211> LENGTH: 17
<212> TYPE: PRT
<213> ORGANISM: Artificial sequence
<220> FEATURE:
<223> OTHER INFORMATION: Hu-H-YE-05-D3 FR2

<400> SEQUENCE: 72

Met Ser Trp Tyr Arg Gln Ala Pro Gly Lys Gly Leu Glu Leu Val Ala
1               5                   10                  15

Val

<210> SEQ ID NO 73
<211> LENGTH: 38
<212> TYPE: PRT
<213> ORGANISM: Artificial sequence
<220> FEATURE:
<223> OTHER INFORMATION: Hu-H-YE-05-D3 FR3

<400> SEQUENCE: 73

Lys Tyr Ser Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
            35

<210> SEQ ID NO 74
<211> LENGTH: 11
<212> TYPE: PRT
<213> ORGANISM: Artificial sequence
<220> FEATURE:
<223> OTHER INFORMATION: Hu-H-YE-05-D3 FR4

<400> SEQUENCE: 74

Trp Gly Gln Gly Thr Gln Val Thr Val Ser Ser
1               5                   10

<210> SEQ ID NO 75
<211> LENGTH: 25
<212> TYPE: PRT
<213> ORGANISM: Artificial sequence
<220> FEATURE:
<223> OTHER INFORMATION: Hu-H-YE-05-D4 FR1

<400> SEQUENCE: 75

Glu Val Gln Leu Leu Glu Ser Gly Gly Gly Leu Val Gln Pro Gly Gly
1               5                   10                  15

Ser Arg Arg Leu Ser Cys Ala Ala Ser
            20                  25
```

-continued

```
<210> SEQ ID NO 76
<211> LENGTH: 17
<212> TYPE: PRT
<213> ORGANISM: Artificial sequence
<220> FEATURE:
<223> OTHER INFORMATION: Hu-H-YE-05-D4 FR2

<400> SEQUENCE: 76

Val Ala Trp Tyr Arg Gln Ala Pro Gly Lys Gln Arg Glu Leu Val Ala
1               5                   10                  15

Val

<210> SEQ ID NO 77
<211> LENGTH: 38
<212> TYPE: PRT
<213> ORGANISM: Artificial sequence
<220> FEATURE:
<223> OTHER INFORMATION: Hu-H-YE-05-D4 FR3

<400> SEQUENCE: 77

Lys Tyr Ser Asp Ser Val Lys Gly Arg Phe Thr Ile Ser Arg Asp Ser
1               5                   10                  15

Ser Lys Asn Thr Val Tyr Leu Gln Met Asn Ser Leu Arg Ala Glu Asp
            20                  25                  30

Thr Ala Val Tyr Tyr Cys
        35

<210> SEQ ID NO 78
<211> LENGTH: 11
<212> TYPE: PRT
<213> ORGANISM: Artificial sequence
<220> FEATURE:
<223> OTHER INFORMATION: Hu-H-YE-05-D4 FR4

<400> SEQUENCE: 78

Trp Gly Gln Gly Thr Gln Val Thr Val Ser Ser
1               5                   10

<210> SEQ ID NO 79
<211> LENGTH: 25
<212> TYPE: PRT
<213> ORGANISM: Artificial sequence
<220> FEATURE:
<223> OTHER INFORMATION: Hu-H-YE-23-D2 FR1

<400> SEQUENCE: 79

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 80
<211> LENGTH: 17
<212> TYPE: PRT
<213> ORGANISM: Artificial sequence
<220> FEATURE:
<223> OTHER INFORMATION: Hu-H-YE-23-D2 FR2

<400> SEQUENCE: 80

Val Ala Trp Tyr Arg Gln Ala Pro Gly Lys Gly Leu Glu Leu Val Ser
1               5                   10                  15

Val

<210> SEQ ID NO 81
```

```
<211> LENGTH: 38
<212> TYPE: PRT
<213> ORGANISM: Artificial sequence
<220> FEATURE:
<223> OTHER INFORMATION: Hu-H-YE-23-D2 FR3

<400> SEQUENCE: 81

Lys Tyr Ser Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 82
<211> LENGTH: 11
<212> TYPE: PRT
<213> ORGANISM: Artificial sequence
<220> FEATURE:
<223> OTHER INFORMATION: Hu-H-YE-23-D2 FR4

<400> SEQUENCE: 82

Trp Gly Gln Gly Thr Leu Val Thr Val Ser Ser
1               5                   10

<210> SEQ ID NO 83
<211> LENGTH: 25
<212> TYPE: PRT
<213> ORGANISM: Artificial sequence
<220> FEATURE:
<223> OTHER INFORMATION: Hu-H-YE-32-D6 FR1

<400> SEQUENCE: 83

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 84
<211> LENGTH: 17
<212> TYPE: PRT
<213> ORGANISM: Artificial sequence
<220> FEATURE:
<223> OTHER INFORMATION: Hu-H-YE-32-D6 FR2

<400> SEQUENCE: 84

Met Ala Trp Tyr Arg Gln Ala Pro Gly Lys Gly Leu Glu Leu Val Ala
1               5                   10                  15

Val

<210> SEQ ID NO 85
<211> LENGTH: 38
<212> TYPE: PRT
<213> ORGANISM: Artificial sequence
<220> FEATURE:
<223> OTHER INFORMATION: Hu-H-YE-32-D6 FR3

<400> SEQUENCE: 85

Gln Tyr Ser Ser Ser Val Lys Gly Arg Phe Thr Ile Ser Arg Asp Asn
1               5                   10                  15

Ser Lys Lys Thr Leu Tyr Leu Gln Met Asn Ser Leu Arg Ala Glu Asp
            20                  25                  30

Thr Ala Val Tyr Tyr Cys
        35
```

-continued

```
<210> SEQ ID NO 86
<211> LENGTH: 11
<212> TYPE: PRT
<213> ORGANISM: Artificial sequence
<220> FEATURE:
<223> OTHER INFORMATION: Hu-H-YE-32-D6 FR4

<400> SEQUENCE: 86

Trp Gly Gln Gly Thr Gln Val Thr Val Ser Ser
1               5                   10

<210> SEQ ID NO 87
<211> LENGTH: 25
<212> TYPE: PRT
<213> ORGANISM: Artificial sequence
<220> FEATURE:
<223> OTHER INFORMATION: Hu-H-YE-32-D5 FR1

<400> SEQUENCE: 87

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 88
<211> LENGTH: 17
<212> TYPE: PRT
<213> ORGANISM: Artificial sequence
<220> FEATURE:
<223> OTHER INFORMATION: Hu-H-YE-32-D5 FR2

<400> SEQUENCE: 88

Met His Trp Tyr Arg Gln Ala Pro Gly Lys Gly Leu Glu Leu Val Ala
1               5                   10                  15

Val

<210> SEQ ID NO 89
<211> LENGTH: 38
<212> TYPE: PRT
<213> ORGANISM: Artificial sequence
<220> FEATURE:
<223> OTHER INFORMATION: Hu-H-YE-32-D5 FR3

<400> SEQUENCE: 89

Tyr Tyr Ala Asp Ser Val Lys Gly Arg Phe Thr Ile Ser Arg Asp Asn
1               5                   10                  15

Ser Lys Lys Thr Leu Tyr Leu Gln Met Asn Ser Leu Arg Ala Glu Asp
            20                  25                  30

Thr Ala Val Tyr Tyr Cys
        35

<210> SEQ ID NO 90
<211> LENGTH: 11
<212> TYPE: PRT
<213> ORGANISM: Artificial sequence
<220> FEATURE:
<223> OTHER INFORMATION: Hu-H-YE-32-D5 FR4

<400> SEQUENCE: 90

Trp Gly Gln Gly Thr Gln Val Thr Val Ser Ser
1               5                   10

<210> SEQ ID NO 91
```

```
<211> LENGTH: 9
<212> TYPE: PRT
<213> ORGANISM: Artificial sequence
<220> FEATURE:
<223> OTHER INFORMATION: linker 1

<400> SEQUENCE: 91

Gly Gly Gly Gly Ser Gly Gly Gly Ser
1               5

<210> SEQ ID NO 92
<211> LENGTH: 2
<212> TYPE: PRT
<213> ORGANISM: Artificial sequence
<220> FEATURE:
<223> OTHER INFORMATION: linker 2

<400> SEQUENCE: 92

Gly Ser
1

<210> SEQ ID NO 93
<211> LENGTH: 5
<212> TYPE: PRT
<213> ORGANISM: Artificial sequence
<220> FEATURE:
<223> OTHER INFORMATION: linker 3

<400> SEQUENCE: 93

Gly Gly Gly Gly Ser
1               5
```

1

NANO-ANTIBODY TARGETING CAIX ANTIGEN AND APPLICATION THEREOF

This application is a National Stage Application under 35 U.S.C. § 371 PCT/CN2020/111112, filed Aug. 25, 2020, which claims priority benefit from Chinese Patent Application No. 201910853699.9, filed on Sep. 10, 2019, the entire contents of each of which is incorporated herein by reference.

SEQUENCE LISTING

The instant application contains a Sequence Listing which has been filed electronically in ASCII format and is hereby incorporated by reference in its entirety. Said ASCII copy, created on May 5, 2022, is named 141279_560361_SL.txt and is 43,285 bytes in size.

TECHNICAL FIELD

The present invention relates to the technical fields of biomedicine or biopharmaceuticals, and more particularly to a nanobody targeting CAIX antigen and its application.

BACKGROUND

CAIX is a transmembrane protein expressed in various solid tumor cells. The main function of CAIX is to maintain the homeostasis of intracellular pH under hypoxic conditions common in solid tumors. The expression of CAIX in tumor cells is considered to be a hypoxic marker protein of the tumor environment and poor prognosis of patients. Common tumor types expressing CAIX include cervical cancer, kidney cancer, brain cancer, head and neck cancer, esophageal cancer, bowel cancer, breast cancer, ovarian cancer, endometrial cancer, bladder cancer, etc. In normal tissues, CAIX is mainly expressed in epithelial cells of bile duct and small intestine, as well as gastric epithelial cells, etc. However, unlike tumor cells, CAIX expressed in normal tissues is mainly localized in the cytoplasm. Therefore, CAIX is an ideal therapeutic target for targeted therapy.

At present, the two fastest-growing antibody drugs targeting CAIX antigen have progressed to the clinical stage. One is Girentuximab, a human-mouse chimeric monoclonal antibody drug developed by Wilex AG, which is currently used for clinical diagnosis of renal cell carcinoma in phase III clinical trials (NCT03849118); the other one is a CAIX-targeting antibody-drug conjugate (CA9-ADC) jointly developed by Bayer AG, Morphosys and Seattle Genetics, whose clinical trial has been advanced to clinical phase I for the clinical treatment of solid tumors. In addition, Dana-Farber Cancer Institute has also developed a CAIX-targeting CAR-T therapy, which is currently in preclinical research.

It has become an urgent problem to develop an anti-CAIX nanobody with better specificity and better clinical efficacy, which can be easily produced with a reduced production cost so as to reduce the medication burden of patients.

CONTENTS OF THE PRESENT INVENTION

The purpose of the present invention is to provide an anti-CAIX single-domain antibody and its application.

Specifically, the purpose of the present invention is to provide a single-domain antibody with good inhibitory effect on solid tumors and good specificity.

The first aspect of the present invention provides a complementarity determining region CDR region of an anti-CAIX single-domain antibody VHH chain, and the complementarity determining region CDR of the VHH chain comprises:

CDR1 shown in SEQ ID NO.5n+1,
CDR2 shown in SEQ ID NO. 5n+2, and
CDR3 shown in SEQ ID NO.5n+3;
wherein each n is independently 0, 1, 2, 3, 4, 5, 6, 7, 8, 9, 10, or 11;
wherein, any one of the above amino acid sequences further comprises a derivative sequence that optionally comprises an addition, deletion, modification and/or substitution of at least one amino acid, and can retain a binding affinity of CAIX.

In another preferred embodiment, the CDR1, CDR2 and CDR3 are separated by framework regions FR1, FR2, FR3 and FR4.

The second aspect of the present invention provides a VHH chain of an anti-CAIX single-domain antibody, wherein the VHH chain comprises a framework region FR and the complementarity determining region CDR described in the first aspect of the present invention.

In another preferred embodiment, the framework region FR comprises:

(a) a FR1 shown in SEQ ID NO.4m+71, a FR2 shown in SEQ ID NO.4m+72, a FR3 shown in SEQ ID NO.4m+73, and a FR4 shown in SEQ ID NO.4m+74; wherein each m is independently 0, 1, 2, 3 or 4.

In another preferred embodiment, the VHH chain of the anti-CAIX single-domain antibody has an amino acid sequence as:

(i) shown in SEQ ID NO.5n+4, wherein each n is independently 0, 1, 2, 3, 4, 5, 6, 7, 8, 9, 10 or 11; or
(ii) shown in SEQ ID NO.2m+61, wherein each m is independently 0, 1, 2, 3 or 4.

In another preferred example, the VHH chain of the anti-CAIX single-domain antibody is shown in SEQ ID NO.4, 9, 14, 19, 24, 29, 34, 39, 44, 49, 54, 59, 61, 63, 65, 67 or 69.

In addition, a heavy chain variable region of an anti-CAIX single-domain antibody is further provided, and the heavy chain variable region comprises:

CDR1 shown in SEQ ID NO.5n+1,
CDR2 shown in SEQ ID NO.5n+2, and
CDR3 shown in SEQ ID NO.5n+3;
wherein each n is independently 0, 1, 2, 3, 4, 5, 6, 7, 8, 9, 10, or 11.

The third aspect of the present invention provides an anti-CAIX single-domain antibody, which is a single-domain antibody against the CAIX epitope and has the VHH chain described in the second aspect of the present invention.

In another preferred example, the anti-CAIX single-domain antibody comprises a monovalent body, a bivalent body (bivalent antibody), and/or a multivalent body (multivalent antibody).

In another preferred embodiment, the anti-CAIX single-domain antibody comprises one or more selected from the follows:

(i) a VHH chain having an amino acid sequence shown in SEQ ID NO.5n+4, wherein each n is independently 0, 1, 2, 3, 4, 5, 6, 7, 8, 9, 10 or 11; and/or
(ii) a VHH chain having an amino acid sequence shown in SEQ ID NO.2m+61, wherein each m is independently 0, 1, 2, 3 or 4.

In another preferred embodiment, the anti-CAIX single-domain antibody comprises a VHH chain having a sequence shown in SEQ ID NO.4, 9, 14, 19, 24, 29, 34, 39, 44, 49, 54, 59, 61, 63, 65, 67 or 69.

In another preferred embodiment, the anti-CAIX single-domain antibody comprises two VHH chains having an amino acid sequence shown in SEQ ID NO.4, 9, 14, 19, 24, 29, 34, 39, 44, 49, 54, 59, 61, 63, 65, 67 or 69.

In another preferred embodiment, the anti-CAIX single-domain antibody has VHH chains with amino acid sequence shown in SEQ ID NO.4, 9, 14, 19, 24, 29, 34, 39, 44, 49, 54, 59, 61, 63, 65, 67 or 69.

In another preferred embodiment, the two VHH chains with amino acid sequence shown in SEQ ID NO.4, 9, 14, 19, 24, 29, 34, 39, 44, 49, 54, 59, 61, 63, 65, 67 or 69 are connected by a linker.

In a preferred embodiment of the present invention, the linker is selected from the following sequences: $(G_aS_b)_x$-$(G_mS_n)_y$, wherein a, b, m, n, x, y=0 or 1 or 2 or 3 or 4 or 5 or 6 or 7 or 8 or 9 or 10 (preferably, a=4 and b=1, m=3 and n=1).

In a preferred embodiment of the present invention, the linker is selected from the group consisting of GGGGSGGGS (SEQ ID NO. 91), GS (SEQ ID NO. 92), GGGGS (SEQ ID NO. 93).

In another preferred embodiment, the amino acid sequence of the anti-CAIX single-domain antibody is shown in SEQ ID NO. 61, 63, 65, 67 or 69.

The fourth aspect of the present invention provides a polynucleotide, the polynucleotide encoding a protein selected from the group consisting of: the CDR region of the anti-CAIX single-domain antibody VHH chain described in the first aspect of the present invention, the VHH chain of anti-CALX single-domain antibody described in the second aspect of the present invention, or the anti-CAIX single-domain antibody described in the third aspect of the present invention.

In another preferred embodiment, the polynucleotide comprises:

(i) a nucleotide sequence shown in SEQ ID NO.5n+5, wherein each n is independently 0, 1, 2, 3, 4, 5, 6, 7, 8, 9, 10 or 11; or (ii) a nucleotide sequence shown in SEQ ID NO.2m+62, wherein each m is independently 0, 1, 2, 3 or 4.

In another preferred embodiment, the polynucleotide has a nucleotide sequence shown in 5, 10, 15, 25, 30, 35, 40, 45, 50, 55, 60, 62, 64, 66, 68 or 70.

In another preferred embodiment, the polynucleotide comprises DNA or RNA.

The fifth aspect of the present invention provides an expression vector, the expression vector comprising the polynucleotide described in the fourth aspect of the present invention.

In another preferred embodiment, the expression vector is selected from the group consisting of DNA, RNA, viral vector, plasmid, transposon, other gene transfer system, or a combination thereof.

Preferably, the expression vector comprises a viral vector, such as lentivirus, adenovirus, AAV virus, retrovirus, or a combination thereof.

The sixth aspect of the present invention provides a host cell, the host cell comprising the expression vector described in the fifth aspect of the present invention, or its genome is integrated with the polynucleotide described in the fourth aspect of the present invention.

In another preferred embodiment, the host cell comprises a prokaryotic cell or eukaryotic cell.

In another preferred embodiment, the host cell is selected from the group consisting of *Escherichia coil*, yeast cell, mammalian cell, bacteriophage, or a combination thereof.

In another preferred embodiment, the prokaryotic cell is selected from the group consisting of *Escherichia coil*, *Bacillus subtilis, Lactobacillus, Streptomyces, Proteus mirabilis*, or a combination thereof.

In another preferred embodiment, the eukaryotic cell is selected from the group consisting of *Pichia pastoris, Saccharomyces cerevisiae, Schizosaccharomyces cerevisiae, Trichoderma*, or a combination thereof.

In another preferred embodiment, the eukaryotic cell is selected from the group consisting of insect cell such as *Mythimna separata*, plant cell such as tobacco, BHK cell, CHO cell, COS cell, myeloma cell, or a combination thereof.

In another preferred embodiment, the host cell is preferably mammalian cell, more preferably HEK293 cell, CHO cell, BHK cell, NSO cell or COS cell.

In another preferred embodiment, the host cell is *Pichia pastoris*.

The seventh aspect of the present invention provides a method for producing an anti-CAIX single-domain antibody, comprising the steps of:

(a) culturing the host cell of the sixth aspect of the present invention under conditions suitable for the production of single-domain antibodies, thereby obtaining a culture containing the anti-CAIN single-domain antibody; and (b) isolating or recovering the anti-CAIX single-domain antibody from the culture; and (c) optionally, purifying and/or modifying the CAIX single-domain antibody obtained in step (b).

In another preferred embodiment, the anti-CAIX single-domain antibody has as SEQ ID NO.4, 9, 14, 19, 24, 29, 34, 44, 49, 54, 59, 61, 63, 65, 67 or 69 shown in the amino acid sequence.

In another preferred embodiment, the anti-CAIX single-domain antibody has the amino acid sequence shown in SEQ ID NO.61, 63, 65, 67 or 69.

The eighth aspect of the present invention provides an immunoconjugate, the immunoconjugate comprises:

(a) the VHH chain of the anti-CAIX single-domain antibody described in the second aspect of the present invention, or the anti-CAIX single-domain antibody described in the third aspect of the present invention; and (b) a conjugation moiety selected from the group consisting of a detectable label, a drug, a toxin, a cytokine, a radionuclide, an enzyme, a gold nanoparticle/nanorod, a nanomagnetic a particle, a viral coat protein or VLP, or combinations thereof.

In another preferred embodiment, the radionuclide comprises:

(i) a diagnostic isotope selected from the group consisting of Tc-99m, Ga-68, F-18, I-123, I-125, I-131, In-111, Ga-67, Cu-64, Zr-89, C-11, Lu-177, Re-188, or a combination thereof; and/or (ii) a therapeutic isotope selected from the group consisting of Lu-177, Y-90, Ac-225, As-211, Bi-212, Bi-213, Cs-137, Cr-51, Co-60, Dy-165, Er-169, Fm-255, Au-198, Ho-166, I-125, I-131, Ir-192, Fe-59, Pb-212, Mo-99, Pd-103, P-32, K-42, Re-186, Re-188, Sm-153, Ra223, Ru-106, Na24, Sr89, Tb-149, Th-227, Xe-133 Yb-169, Yb-177, or a combination thereof.

In another preferred embodiment, the conjugation moiety is a drug or a toxin.

In another preferred embodiment, the drug is a cytotoxic drug.

In another preferred embodiment, the cytotoxic drug is selected from the group consisting of anti-tubulin drug, DNA minor groove binding reagent, DNA replication inhibitor, alkylating reagent, antibiotic, folic acid antagonist, anti-metabolite, chemosensitizer, topoisomerase inhibitor, vinca alkaloid, or a combination thereof.

In another preferred embodiment, examples of particularly useful cytotoxic drug include, for example, DNA minor groove binding reagent, DNA alkylating reagent, and tubulin inhibitor; and typical cytotoxic drugs include, for example, auristatins, camptothecins, duocarmycins, etoposides, maytansines and maytansinoids (e.g., DM1 and DM4)), taxanes, benzodiazepines, or benzodiazepine-containing drugs (e.g., pyrrolo[1,4]benzodiazepines (PBDs), indolinobenzodiazepines and oxazolidinobenzodiazepines), vinca alkaloids, or combinations thereof.

In another preferred embodiment, the toxin is selected from the group consisting of: auristatin (e.g., auristatin E, auristatin F, MMAE and MMAF), chlortetracycline, maytansinoid, ricin, ricin A-chain, combretastatin, duocarmycins, dolastatin, doxorubicin, daunorubicin, paclitaxel, cisplatin, cc1065, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, volkensin toxin A chain, α-sarcines, gelonin, mitogellin, retstrictocin, phenomycin, enomycin, curicin, crotin, calicheamicin, *Sapaonaria officinalis* inhibitor, glucocorticoid, or a combination thereof.

In another preferred embodiment, the conjugation moiety is a detectable label.

In another preferred embodiment, the conjugation moiety is selected from the group consisting of fluorescent or luminescent label, radiolabel, MRI (magnetic resonance imaging) or CT (computed tomography) contrast agent, or enzyme capable of producing detectable product, radionuclide, biotoxin, cytokine (such as IL-2, etc.), antibody, antibody Fc fragment, antibody scFv fragment, gold nanoparticle/nanorod, virus particle, liposome, nanomagnetic particle, prodrug-activating enzyme (e.g., DT-diaphorase (DTD) or biphenyl hydrolase-like protein (BPHL)), chemotherapeutic agent (e.g., cisplatin), or nanoparticle in any form.

In another preferred embodiment, the immunoconjugate comprises: the VHH chain of the anti-CAIX single-domain antibody described in the second aspect of the present invention or the anti-CAIX single-domain antibody described as described in the third aspect of the present invention that is multivalent (e.g., bivalent).

In another preferred embodiment, the multivalent refers to that the amino acid sequence of the immunoconjugate comprises multiple repeats of the VHH chain of the anti-CAIX single-domain antibody described in the second aspect of the present invention, or the anti-CAIX single-domain antibody as described in the third aspect of the present invention.

The ninth aspect of the present invention provides a use of the anti-CAIX single-domain antibody VHH chain described in the second aspect of the present invention or the anti-CAIX single-domain antibody described in the third aspect of the present invention, in the manufacture of:

(a) a CAIX antigen-targeting-related antibody-drug conjugate (ADC), a monoclonal antibody drug, a bispecific/multispecific antibody drug, or a cell therapy-related drug; or

(b) a medicament for the diagnosis or treatment of a CAIX-associated disease or condition.

A tenth aspect of the present invention provides a pharmaceutical composition, the pharmaceutical composition comprising:

(i) the complementarily determining region CDR region of the anti-CAIX single-domain antibody VHH chain described in the first aspect of the present invention, the VHH chain of the anti-CAIX single-domain antibody described in the second aspect of the present invention, the anti-CAIX single-domain antibody described in the third aspect, or the immunoconjugate described in the eighth aspect of the present invention; and (ii) a pharmaceutically acceptable carrier.

In another preferred embodiment, the conjugation part of the immunoconjugate is a drug, a toxin, and/or a therapeutic isotope.

In another preferred embodiment, the pharmaceutical composition further comprises an additional drug for treating a tumor, such as a cytotoxic drug.

In another preferred embodiment, the pharmaceutical composition is in the form of injection.

In another preferred embodiment, the pharmaceutical composition is used for the manufacture of a medicament for the treatment of a CAIX-associated disease or condition, and the disease or condition includes tumor or cancer.

In another preferred example, the tumor or cancer includes but is not limited to one or more selected to from the group consisting of: cervical cancer, kidney cancer, brain cancer, head and neck cancer, esophageal cancer, bowel cancer, breast cancer, ovarian cancer, endometrial cancer, bladder cancer.

The eleventh aspect of the present invention provides a use of the anti-CAIX single-domain antibody described in the third aspect of the present invention:

(a) in manufacture of a CAIX antigen-targeting-related antibody-drug conjugate (ADC), a monoclonal antibody drug, a bispecific/multispecific antibody drug, or a cell therapy-related drug, etc.;

(b) in manufacture of a medicament for the diagnosis or treatment of a CAIX-associated disease or condition;

(c) for the detection of a human CAIX molecule;

(d) for a flow cytometry;

(e) for a cell immunofluorescent detection;

(f) for the treatment of a tumor;

(g) for the diagnosis of a tumor.

In another preferred embodiment, the use is diagnostic and/or non-diagnostic, and/or therapeutic and/or non-therapeutic.

The twelfth aspect of the present invention provides an antibody, the antibody comprising one or more the VHH chain(s) of the anti-CAIX single-domain antibody described in the second aspect of the present invention.

In another preferred embodiment, the antibody comprises two VHH chains of the anti-CAIX single-domain antibody described in the second aspect of the present invention.

In another preferred embodiment, the antibody has the heavy chain variable region VHH as described in the second aspect of the present invention.

In another preferred embodiment, the antibody is a single-domain antibody.

In another preferred embodiment, the antibody is a bispecific antibody (which simultaneously targets CAIX and another tumor-related antigen or immune cell activation-related antigen, etc.).

In another preferred embodiment, the antibody is a multispecific antibody (which simultaneously targets CAIX and other tumor-related antigens or immune cell activation-related antigens).

The thirteenth aspect of the present invention provides a recombinant protein, the recombinant protein comprises:

(i) the VHH chain described in the second aspect of the present invention or the anti-CAIX single-domain antibody described in to the third aspect of the present invention; and (ii) optionally, a tag sequence for facilitating expression and/or purification.

In another preferred embodiment, the tag sequence comprises Fc tag, HA tag and 6His tag.

In another preferred embodiment, the recombinant protein specifically binds to CAIX protein.

The fourteenth aspect of the present invention provides a use of the VHH chain of the anti-CAIX single-domain antibody described in the second aspect of the present invention, the anti-CAIX single-domain antibody described in the third aspect of the present invention, or the immunoconjugate described in the eighth aspect of the present invention, in the manufacture of a medicament, reagent, detection plate or kit;

wherein, the reagent, detection plate or kit is used for the detection of a CAIX protein in a sample;

wherein, the medicament is used for the treatment or prevention of a CAIX-associated disease or condition.

In another preferred embodiment, the detection comprises flow cytometry detection and cellular immunofluorescence detection.

In another preferred embodiment, the disease or condition comprises a tumor or cancer.

In another preferred example, the tumor or cancer includes but is not limited to one or more selected from the group consisting of: cervical cancer, kidney cancer, brain cancer, head and neck cancer, esophageal cancer, bowel cancer, breast cancer, ovarian cancer, endometrial cancer, bladder cancer.

The fifteenth aspect of the present invention provides a method for treating a disease, the method comprising administering to a subject in need thereof the single-domain antibody described in the third aspect of the present invention, or the immunoconjugate described in the eighth aspect of the present invention.

In another preferred embodiment, the subject comprises a mammal, such as human, mouse, rabbit, and monkey.

The sixteenth aspect of the present invention provides a method for detecting a CAIX protein in a sample, the method comprising the steps of:

(1) contacting the sample with the VHH chain described in the second aspect of the present invention, the single-domain antibody described in the third aspect of the present invention, or the immunoconjugate described in the eighth aspect of the present invention;

(2) detecting whether an antigen-antibody complex is formed, wherein the formation of the complex indicates the presence of the CAIX protein in the sample.

In another preferred embodiment, the method is a non-diagnostic and/or non-therapeutic method.

The seventeenth aspect of the present invention provides a CAIX protein detection reagent, the detection reagent comprising:

(i) the VHH chain described in the second aspect of the present invention, the single-domain antibody described in the third aspect of the present invention, or the immunoconjugate described in the eighth aspect of the present invention; and (ii) a detectably acceptable carrier.

In another preferred embodiment, the conjugation part of the immunoconjugate is a diagnostic isotope.

In another preferred embodiment, the detectably acceptable carrier is a non-toxic, inert aqueous carrier medium.

In another preferred embodiment, the detection reagent is one or more reagents selected from the group consisting of isotope tracer, contrast agent, flow detection reagent, cellular immunofluorescence detection reagent, magnetic nanoparticle and imaging agent.

In another preferred embodiment, the detection reagent is used for in vivo detection.

In another preferred embodiment, the detection reagent is in a dosage form of liquid or powder (e.g., water preparation, injection, freeze-dried powder, tablet, buccal preparation, aerosol preparation).

The eighteenth aspect of the present invention provides a kit for detecting a CAIX protein, the kit comprising the immunoconjugate described in the eighth aspect of the present invention or the detection reagent described in the seventeenth aspect of the present invention, and an instruction manual.

In another preferred embodiment, the instruction manual describes that the kit is used to non-invasive detection of an expression of CAIX in a subject to be tested.

The nineteenth aspect of the present invention provides a use of the immunoconjugate described in the eighth aspect of the present invention in manufacture of a contrast agent for the detection of a CAIX protein in vivo.

In another preferred embodiment, the detection is used for the diagnosis or prognosis of a cancer.

The twentieth aspect of the present invention provides a CAR-T cell, the CAR-T cell expressing a chimeric antigen receptor CAR, and the CAR has an antigen-binding domain comprising VHH chain of the anti-CAIX single-domain antibody described in the second aspect of the present invention, or the anti-CALX single-domain antibody described in the third aspect of the present invention.

The twenty-first aspect of the present invention provides a preparation, the preparation comprising the CAR-T cell described in the twentieth aspect of the present invention, and a pharmaceutically acceptable carrier, diluent or excipient.

In another preferred embodiment, the preparation is a liquid preparation.

In another preferred embodiment, the preparation is in a dosage form comprising injection.

In another preferred example, the CAR-T cells in the preparation has a concentration of $1 \times 10^3$ to $1 \times 10^8$ cells/ml, preferably $1 \times 10^4$ to $1 \times 10^7$ cells/ml.

The twenty-second aspect of the present invention provides a VHH chain framework region FR of an anti-CAIX single-domain antibody, wherein the VHH chain framework region FR consists of:

(a) a FR1 shown in SEQ ID NO.4m+71, a FR2 shown in SEQ ID NO.4m+72, a FR3 shown in SEQ ID NO.4m+73, and a FR4 shown in SEQ ID NO.4m+74, wherein each in is independently 0, 1, 2, 3 or 4.

The twenty-third aspect of the present invention provides a method for treating a CAIX-associated disease or condition, comprising administering to a subject in need thereof the pharmaceutical composition described in the tenth aspect of the present invention.

In another preferred embodiment, the subject comprises a mammal, such as human.

It should be understood that within the scope of the present invention, the above-mentioned technical features of the present invention and the technical features specifically described in the following (e.g., the examples) can be combined with each other to form new or preferred technical solutions. Due to space limitations, it is not repeated here.

SPECIFIC MODELS FOR CARRYING OUT THE PRESENT INVENTION

Figure 1:
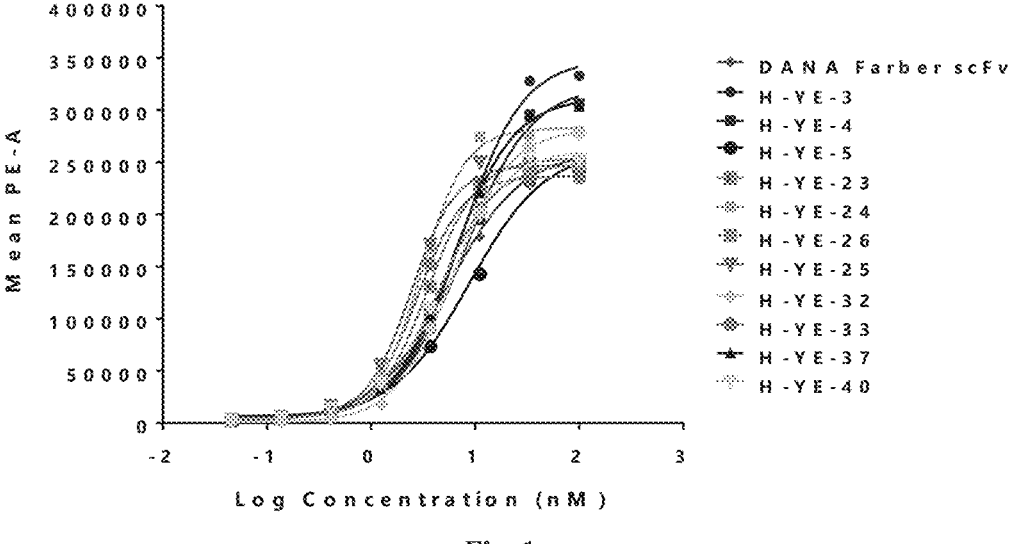
FIG. 1 shows the diagram of detection results of the binding capacity of CAIX nanobodies to CHO-hCAIX at cell level.

After extensive and in-depth research and extensive screening, the inventors of the present invention unexpectedly discovered a class of anti-CAIX single-domain antibodies for the first time. The experimental results show that the single-domain antibodies of the present invention can specifically recognize CAIX, and can bind with high affinity to CAIX protein or CAIX-positive cells. It is easy to generate the single-domain antibody of the present invention. Thus, the present invention has been completed.

Specifically, in the present invention, after immunizing alpacas with CAIX antigen, the RNA in the peripheral lymphocytes of the alpacas was extracted and inverted into cDNA to construct a yeast screening library of CAIX nanobodies. The yeast library was screened by magnetic beads and enriched by flow cytometry to obtain CAIX-specific binding antibodies. The antibody obtained from the preliminary screening was expressed and prepared, and the affinities of the CAIX antigen at the protein level and the cell level were determined, respectively, which laid the foundation for the next step of drug development.

Terms

As used herein, the terms "single-domain antibody of the present invention", "anti-CAIX antibody of the present invention", "CAIX single-domain antibody of the present invention", "anti-CAIX single-domain antibody" have the same meaning, and can be used interchangeably, which all refer to a single-domain antibody that specifically recognizes and hinds to CAIX (including human CAIX). Preferably, the variable region of the single-domain antibody of the present invention has a CDR1 shown in SEQ ID NO.5n+ 1, a CDR2 shown in SEQ ID NO.5n+2, and a CDR3 shown in SEQ ID NO.5n+3, wherein each n is independently 0, 1, 2, 3, 4, 5, 6, 7, 8, 9, 10 or 11. More preferably, the amino acid sequence of the VHH chain of the single-domain antibody of the present invention is shown in: (i) SEQ ID NO.5n+4, wherein each n is independently 0, 1, 2, 3, 4, 5, 6, 7, 8, 9, 10 or 11; or (ii) SEQ ID NO. 2m+61, wherein each m is independently 0, 1, 2, 3 or 4. Still more preferably, the framework region of the single-domain antibody of the present invention has (a) a FR1 shown in SEQ ID NO.4m+ 71, a FR2 shown in SEQ ID NO.4m+72, and a FR3 shown in SEQ ID NO.4m+73, and a FR4 shown in SEQ ID NO.4m+74; wherein each m is independently 0, 1, 2, 3 or 4.

As used herein, the term "antibody" or "immunoglobulin" is a heterotetramer of glycoproteins of about 150,000 Daltons having the same structural characteristics, and consists of two identical light (L) chains and two identical heavy chains (H). Each light chain is linked to the heavy chain by a covalent disulfide bond, and the number of disulfide bonds varies between heavy chains of different immunoglobulin isotypes. Each heavy and light chain also has regularly spaced intrachain disulfide bridges. At one end of each heavy chain is a variable region (VH) followed by a number of constant regions. Each light chain has a variable domain (VL) at one end and a constant domain at the other end; the constant domain of light chain is opposite to the first constant domain of heavy chain, and the variable domain of light chain is opposite to the variable domain of heavy chain. Particular amino acid residues form the interface between the variable regions of the light and heavy chains.

As used herein, the terms "single-domain antibody", "VHH", "nanobody", "single domain antibody" (sdAb, or nanobody) have the same meaning and are used interchangeably, and refers to heavy chain variable region of cloning antibody, a single-domain antibody (VHH) constructed with only one heavy chain variable region by cloning antibody heavy chain variable region, which is the smallest antigen-binding fragment with complete functions. Usually, an antibody that naturally lacks light chain and heavy chain constant region 1 (CH1) is obtained first, and then the variable region of the antibody heavy chain is cloned to construct a single-domain antibody (VHH) consisting of only one heavy chain variable region.

As used herein, the term "variable" means that certain portions of variable regions of antibody differ in sequence, which contributes to the binding and specificity of each particular antibody for its particular antigen. However, the variability is not evenly distributed throughout the antibody variable region. It is concentrated in three segments called complementarity determining regions (CDRs) or hypervariable regions in the light and heavy chain variable regions. The more conserved parts of the variable regions are called framework regions (FRs). The variable regions of native heavy and light chains each contain four FR regions, which are roughly-folded in β-configuration, linked by three CDRs that form a linking loop; in some cases, a partially folded β-configuration could be formed. The CDRs in each chain are tightly packed together by the FR regions and together with the CDRs of the other chain form the antigen-binding site of the antibody (see Kabat et al., NIH Publ. No. 91-3242, Vol. 1, pp. 647-669 (1991)). The constant regions are not directly involved in the binding of the antibody to the antigen, but they exhibit different effector functions, such as involvement in antibody-dependent cytotoxicity of the antibody.

As known to those skilled in the art, immunoconjugate and fusion expression product includes a conjugates that is formed by binding a drug, toxin, cytokine, radionuclide, enzyme and other diagnostic or therapeutic molecule to the antibody of the present invention or fragment thereof. The present invention also comprises a cell surface marker or antigen that binds to the anti-CAIX antibody or fragment thereof.

As used herein, the terms "heavy chain variable region" and "VH" are used interchangeably.

As used herein, the terms "variable region" and "complementarity determining region (CDR)" are used interchangeably.

In a preferred embodiment of the present invention, the heavy chain variable region of the antibody comprises three complementarity determining regions CDR1, CDR2, and CDR3.

In a preferred embodiment of the present invention, the heavy chain of the antibody comprises the above-mentioned heavy chain variable region and heavy chain constant region.

In the present invention, the terms "antibody of the present invention", "protein of the present invention", or "polypeptide of the present invention" are used interchangeably, and all refer to a polypeptide that specifically binds to a CAIX protein, such as a protein or polypeptide having a heavy chain variable region. They may or may not contain a starting methionine.

The present invention also provides another protein or fusion expression product having the antibody of the present invention. Specifically, the present invention comprises any protein or protein conjugate and fusion expression product (i.e., immunoconjugate and fusion expression product) having a variable region-containing heavy chain, as long as the variable region is identical or at least 90% homologous, preferably at least 95% homologous to the heavy chain variable region of the antibody of the present invention.

Generally, the antigen-binding properties of an antibody can be described by three specific regions located in its heavy chain variable region, called variable regions (CDRs), which is separated into four framework regions (FRs), while the four FR amino acid sequences are relatively conservative and do not directly participate in the binding reaction. These CDRs form a circular structure, and the β-sheets formed by the FRs in between are spatially close to each other, and the CDRs on the heavy chain and the CDRs on the corresponding light chain constitute the antigen-binding site of the antibody. By comparison with the amino acid sequence of the same type of antibody, it can determine which amino acids make up the FR or CDR regions.

The heavy chain variable regions of the antibodies of the present invention are of particular interest because at least some of them are involved in binding antigen. Thus, the present invention comprises those molecules having CDR-bearing antibody heavy chain variable regions, as long as their CDRs are more than 90% (preferably more than 95%, optimally more than 98%) homologous to the CDRs identified herein.

The present invention comprises not only an intact antibody, but also an antibody fragment with immune activity or a fusion protein formed by the antibody with other sequences. Accordingly, the present invention further comprises a fragment, derivative and analog of the antibody.

As used herein, the terms "fragment", "derivative" and "analog" refer to a polypeptide that retains substantially the same biological function or activity of the antibody of the present invention. The polypeptide fragment, derivative or analog of the present invention may be (i) a polypeptide having a substitution of one or more conservative or non-conservative amino acid residues (preferably conservative amino acid residues), and such substitution of amino acid residues may or may not be encoded by a genetic code, or (ii) a polypeptide having one or more amino acid residues with a substituent group, or (iii) a mature polypeptide formed by the fusion of a mature polypeptide with another compound (e.g., a compound that prolongs the half-life of the polypeptide, e.g. polyethylene glycol), or (iv) a polypeptide formed by the fusion of an additional amino acid sequence to the polypeptide sequence (e.g., a fusion protein formed with a leader sequence or a secretory sequence or a sequence used to purify the polypeptide or a proprotein sequence, or with 6His-tag). These fragments, derivatives and analogs are well known to those skilled in the art in light of the teachings herein.

The antibody of the present invention refers to a polypeptide comprising the above-mentioned CDR region and having the CAIX-binding activity. The term also comprises variant forms of the polypeptides comprising the above-mentioned CDR regions and having the same function as the antibody of the present invention. These variants include (but are not limited to): deletion, insertion and/or substitution of one or more (usually 1-50, preferably 1-30, more preferably 1-20, most preferably 1-10) amino acids, and addition of one or several (usually within 20, preferably within 10, more preferably within 5) amino acids at the C-terminus and/or N-terminus. For example, in the art, substitution with amino acids of similar properties generally does not alter the function of the protein. As another example, the addition of one or more amino acids to the C-terminus and/or N-terminus generally does not alter the function of the protein. The term also comprises an active fragment and an active derivative of the antibody of the present invention.

The variant forms of the polypeptide comprise: homologous sequences, conservative variants, allelic variants, natural mutants, induced mutants, proteins encoded with a DNA capable of hybridizing with the DNA encoding the antibody of the present invention under conditions of high or low stringency, and polypeptides or proteins obtained using an antiserum against the antibody of the present invention.

The present invention also provides an additional polypeptide, such as a fusion protein comprising a single-domain antibody or fragment thereof. In addition to nearly full-length polypeptide, the present invention also comprises a fragment of the single-domain antibody of the present invention. Typically, the fragment has at least about 50 contiguous amino acids, preferably at least about 50 contiguous amino acids, more preferably at least about 80 contiguous amino acids, and most preferably at least about 100 contiguous amino acids of the antibody of the present invention.

In the present invention, "conservative variant of the antibody of the present invention" means a polypeptide formed by substitution of at most 10, preferably at most 8, more preferably at most 5, and most preferably at most 3 amino acids with similar properties, in comparison with the amino acid sequence of the antibody of the present invention. These conservative variant polypeptides are best produced by amino acid substitutions according to Table 1.

TABLE 1

| Original residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |

TABLE 1-continued

| Original residue | Representative substitution | Preferred substitution |
|---|---|---|
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide molecule encoding the above-mentioned antibody or fragment or fusion protein thereof. The polynucleotide of the present invention may be in the form of DNA or RNA. DNA forms include cDNA, genomic DNA or synthetic DNA. The DNA can be single-stranded or double-stranded. The DNA can be a coding or non-coding strand.

The polynucleotide encoding the mature polypeptide of the present invention comprises: coding sequence encoding only the mature polypeptide; coding sequence and various additional coding sequences for the mature polypeptide; coding sequence (and optional additional coding sequences) for the mature polypeptide and non-coding sequences.

The term "polynucleotide encoding polypeptide" may comprises a polynucleotide encoding the polypeptide or a polynucleotide that further comprises an additional coding and/or non-coding sequence.

The present invention also relates to polynucleotide that hybridizes to the above-mentioned sequence and has at least 50%, preferably at least 70%, more preferably at least 80% identity between the two sequences. In particular, the present invention relates to a polynucleotide that is hybridizable to the polynucleotide of the present invention under stringent conditions. In the present invention, "stringent conditions" refer to: (1) hybridization and elution at lower ionic strength and higher temperature, such as 0.2×SSC, 0.1% SDS, 60° C.; or (2) hybridization is performed by adding a denaturing agent, such as 50% (v/v) formamide, 0.1% calf serum/0.1% Ficoll, 42° C., etc.; or (3) hybridization occurs only when the identity between the two sequences is at least 90% or more, more preferably at least 95%. Furthermore, the polypeptide encoded by the hybridizable polynucleotide has the same biological function and activity as the mature polypeptide.

The full-length nucleotide sequence of the antibody of the present invention or its fragment can usually be obtained by PCR amplification method, recombinant method or artificial synthesis method. A feasible method is to use artificial synthesis to synthesize the relevant sequences, especially when the fragment length is short. Usually, fragments of very long sequences are obtained by synthesizing multiple small fragments followed by ligation. In addition, the coding sequence of the heavy chain and the expression tag (such as 6His) can also be fused together to form a fusion protein.

Once the relevant sequences have been obtained, recombinant methods can be used to obtain the relevant sequences in bulk. This is usually done by cloning them into a vector, transferring into a cell, and isolating the relevant sequences from the propagated host cells by conventional methods. Biomolecules (nucleic acids, proteins, etc.) referred to in the present invention include biomolecules in isolated forms.

At present, the DNA sequence encoding the protein of the present invention (or fragment thereof, or derivative thereof can be obtained entirely by chemical synthesis. This DNA sequence can then be introduced into various existing DNA molecules (or, e.g., vectors) and cells known in the art. In addition, a mutation can also be introduced into the protein sequence of the present invention by chemical synthesis.

The present invention also relates to a vector comprising a suitable DNA sequence as described above together with a suitable promoter or a control sequence. Such vector can be used to transform an appropriate host cell so as to express the protein.

The host cell can be a prokaryotic cell, such as bacterial cell; or lower eukaryotic cell, such as yeast cell; or higher eukaryotic cell, such as mammalian cell. Representative examples are: *Escherichia coli, Streptomyces*; bacterial cell of *Salmonella typhimurium*; fungal cell such as yeast; insect cell of *Drosophila* S2 or Sf9; animal cell such as CHO, COS7, 293 cells, etc.

Transformation of host cells with recombinant DNA can be performed using conventional techniques well known to those skilled in the art. When the host is a prokaryotic organism such as *E. coli*, competent cells capable of uptaking DNA can be harvested after exponential growth phase and treated by the CaCl$_2$ method, in which the used procedures are well known in the art. Another method is to use MgCl$_2$. If desired, transformation can also be performed by electroporation. When the host is an eukaryotic organism, the following DNA transfection methods can be used: calcium phosphate co-precipitation method, conventional mechanical methods such as microinjection, electroporation, liposome packaging, etc.

The obtained transformants can be cultured by conventional methods to express the polypeptide encoded by the gene of the present invention. The medium used in the culture can be selected from various conventional media depending on the host cells used. Cultivation is carried out under conditions suitable for growth of the host cells. After the host cells have grown to an appropriate cell density, the promoter of choice is induced by a suitable method (e.g., temperature switching or chemical induction), and the cells are cultured for an additional period of time.

The recombinant polypeptide in the above method can be expressed intracellularly, or on the cell membrane, or secreted outside the cell, if desired, the recombinant protein can be isolated and purified by various isolation methods utilizing its physical, chemical and other properties. These methods are well known to those skilled in the art. Examples of these methods include, but are not limited to: conventional renaturation treatment, treatment with protein precipitants (salting-out method), centrifugation, osmotic disruption, ultrasonic treatment, ultracentrifugation, molecular sieve chromatography (gel filtration), adsorption chromatography, ion exchange chromatography, high performance liquid chromatography (HPLC) and various other liquid chromatography techniques, and combinations of these methods.

The antibody of the present invention may be used alone, or may be combined or conjugated to a detectable label (for diagnostic purposes), a therapeutic agent, a PK (protein kinase) modifying moiety, or a combination of any of the above.

The detectable label for diagnostic purposes includes, but is not limited to, fluorescent or luminescent label, radiolabel, MRI (magnetic resonance imaging) or CT (computed tomography) contrast agent, or enzyme capable of producing a detectable product.

The therapeutic agent capable of being combined or conjugated with the antibody of the present invention includes, but is not limited to: 1. radionuclide; 2. biotoxin; 3. cytokine such as IL-2, etc.; 4. gold nanoparticle/nanorod; 5. virus particle; 6. liposome; 7. nanomagnetic particle; 8.

prodrug-activating enzyme (e.g., DT-diaphorase (DTD) or biphenyl hydrolase-like protein (BPHL)); 10. chemotherapeutic agent (e.g., cisplatin) or any form of nanoparticles, etc.

CAIX

CAIX is a transmembrane protein expressed in various solid tumor cells. The main function of CAIX is to maintain the homeostasis of intracellular pH under hypoxic conditions common in solid tumors. Human CAIX has a molecular weight of 49.7 KDa and consists of 459 amino acids. CAIX is a type I transmembrane protein comprising a signal peptide, a glycoprotein-like domain, a carbonic anhydrase-base domain, a transmembrane domain, and an intracellular domain. Among them, the extracellular carbonic anhydrase-base domain is the enzymatic region that regulates intracellular pH homeostasis.

Pharmaceutical Composition

The present invention also provides a composition. Preferably, the composition is a pharmaceutical composition, which comprises the above-mentioned antibody or its active fragment or its fusion protein, and a pharmaceutically acceptable carrier. Generally, these materials can be formulated in a non-toxic, inert and pharmaceutically acceptable aqueous carrier medium, usually at a pH of about 5-8, preferably at a pH of about 6-8, although the pH may vary depending on the nature of the formulated materials and the disease and condition to be treated. The obtained pharmaceutical composition can be administered by a conventional route including, but not limited to, intratumoral, intraperitoneal, intravenous, or topical administration.

The pharmaceutical composition of the present invention can be directly used to bind a CAIX protein molecule, and thus can be used to treat a tumor. In addition, an additional therapeutic agent may also be used concomitantly.

The pharmaceutical composition of the present invention comprises a safe and effective amount (such as 0.001-99 wt %, preferably 0.01-90 wt %, more preferably 0.1-80 wt %) of the above-mentioned single-domain antibody (or its conjugate) of the present invention and a pharmaceutically acceptable carrier or excipient. Such carrier includes (but is not limited to): saline, buffer, dextrose, water, glycerol, ethanol, and combination thereof. Pharmaceutical preparation should match the mode of administration. The pharmaceutical composition of the present invention can be prepared in the form of injection, for example, prepared by conventional methods with physiological saline or an aqueous solution containing glucose and other adjuvants. The pharmaceutical compositions in the forms of injections and solutions can be preferably manufactured under sterile conditions. The active ingredient is administered in a therapeutically effective amount, e.g., about 10 μg/kg body weight to about 50 mg/kg body weight per day. In addition, the polypeptide of the present invention may also be used with an additional therapeutic agent.

When the pharmaceutical composition is used, a safe and effective amount of the immunoconjugate is administered to a mammal, wherein the safe and effective amount is generally at least about 10 μg/kg body weight, and in most cases no more than about 50 mg/kg body weight; preferably, the dose is about 10 μg/kg body weight to about 10 mg/kg body weight. Of course, the specific dose should also take into account the route of administration, the patient's health and other factors, which are all within the skill of the skilled physician.

Anti-CAIX Single-Domain Antibody

In the present invention, the anti-CAIX single-domain antibody comprises monovalent, bivalent (bivalent antibody), and/or multivalent (multivalent antibody).

In a preferred embodiment of the present invention, the anti-CAIX single-domain antibody comprises one, two or more copies as the follows:
(i) a VHH chain having an amino acid sequence shown in SEQ ID NO.5n+4, wherein each n is independently 0, 1, 2, 3, 4, 5, 6, 7, 8, 9, 10 or 11; and/or
(ii) a VHH chain having an amino acid sequence shown in SEQ ID NO.2m+61, wherein each m is independently 0, 1, 2, 3 or 4.

Typically, the anti-CAIX single-domain antibody comprises two copies of a VHH chain having an amino acid sequence shown in SEQ ID NO.4, 9, 14, 19, 24, 29, 34, 39, 44, 49, 54, 59, 61, 63, 65, 67 or 69.

Typically, the anti-CAIX single-domain antibody has a VHH chain having an amino acid sequence shown in SEQ ID NO4, 9, 14, 19, 24, 29, 34, 39, 44, 49, 54, 59, 61, 63, 65, 67 or 69.

In a preferred example of the present invention, the two copies of the VHH chain having an amino acid sequence shown in SEQ ID NO.4, 9, 14, 19, 24, 29, 34, 39, 44, 49, 54, 59, 61, 63, 65, 67 or 69 are connected by a linker.

In a preferred embodiment of the present invention, the linker is selected from the following sequence: $(G_aS_b)_x$-$(G_mS_n)_y$, wherein a, b, m, n, x, y=0 or 1 or 2 or 3 or 4 or 5 or 6 or 7 or 8 or 9 or 10 (preferably, a=4 and b=1, m=3 and n=1).

In a preferred embodiment of the present invention, the linker is selected from the group consisting of GGGGSGGGS (SEQ ID NO. 91), GS (SEQ ID NO. 92), GGGGS (SEQ ID NO. 93).

In another preferred embodiment, the amino acid sequence of the anti-CAIX single-domain antibody is shown in SEQ ID NO. 61, 63, 65, 67 or 69.

Labeled Single-Domain Antibody

In a preferred embodiment of the present invention, the single-domain antibody has a detectable label. More preferably, the label is selected from the group consisting of isotope, colloidal gold label, colored label or fluorescent label.

Colloidal gold labeling can be performed using methods known to those skilled in the art. In a preferred solution of the present invention, the anti-CAIX single-domain antibody is labeled with colloidal gold to obtain a colloidal gold-labeled single-domain antibody.

The anti-CAIX single-domain antibody of the present invention has good specificity and high titer.

Detection Method

The present invention also relates to a method for detecting a CAIX protein. The method comprises steps roughly as follows: obtaining a cell and/or tissue sample; lysing the sample in a medium; detecting a level of CAIX protein in the lysed sample.

In the detection method of the present invention, the sample to be used is not particularly limited, and a representative example thereof is a cell-containing sample existing in a cell preservation solution.

Kit

The present invention also provides a kit comprising the antibody (or fragment thereof) or detection plate of the present invention. In a preferred embodiment of the present invention, the kit further comprises a container, an instruction manual, a buffer, and the like.

The present invention also provides a detection kit for detecting the level of CAIX, the kit comprises an antibody that recognizes CAIX protein, a lysis medium for dissolving the sample, general reagents and buffers required for detection, such as various buffers, detection labels, detection substrates, etc. The detection kit may be an in vitro diagnostic device.

Application

As mentioned above, the single-domain antibody of the present invention has a value for wide range of biological applications and clinical applications, and its application involves the diagnosis and treatment of CAIX-associated diseases, basic medical research, biological research and other fields. A preferred application is for clinical diagnosis and targeted therapy against CAIX.

The Main Advantages of the Present Invention Include (a) the single-domain antibody of the present invention has a small molecular weight and good stability.
(b) compared with traditional common normal antibodies, the single-domain antibody of the present invention has many advantages, such as good tissue infiltration, flexible administration mode, high degree of humanization, and easy recombinant protein transformation in drug development and diagnostic reagent development, etc.;
(c) the production of the single-domain antibody of the present invention is simple.

The following specific examples further illustrate the present invention. It should be understood that these examples are only used to illustrate the present invention and not to limit the scope of the present invention. The experimental methods without specific conditions in the following examples were performed usually according to conventional conditions, for example the conditions descried in Sambrook and Russell, et al., Molecular Cloning-A Laboratory Manual, third edition, (2001) CSHL publishes Society, or as recommended by the manufacturer. Percentages and parts are by weight unless otherwise indicated.

Example 1

Immunization and Screening of CAIX Nanobody

After immunizing alpaca (Llama) with human CAIX antigen (purchased from AcroBiosystems), the total RNA in the peripheral lymphocytes of the alpaca was extracted and reversed into cDNA. The PCR product of the cDNA was ligated with a yeast display vector and electrotransformed into *Saccharomyces cerevisiae* (Purchased from ATCC), and the CAIX nanobody library was constructed.

The CAIX protein (purchased from AcroBiosystems) was labeled according to the product instructions of the biotin labeling kit (purchased from Thermo). After the amplified CAIX nanobody yeast library was labeled with biotin-labeled CAIX protein, magnetic beads were used to enrich the positively labeled yeast. After the yeast cells enriched with magnetic beads were proliferated, 1:200 diluted anti-c-Myc antibody (purchased from Thermo) and an appropriate amount of biotin-labeled CAIX antigen were added for staining. After washing the yeast with PBS, 1:500 diluted goat-Anti-mouse IgG(H+L) Alexa Fluor Plus 488 (purchased from Invitrogen) and streptavidin APC conjugate fluorescent antibody (purchased from Invitrogen) were added, incubated for 15 min. The cells were resuspended in PBS and sorted using a BD FACSAria II instrument to obtain yeast with higher binding ability to PD-L1 antigen.

The yeast liquid with high binding ability to CAIX antigen obtained by sorting and enrichment through magnetic beads and flow cytometry was cultured overnight in amplification medium at 30° C. and 225 rpm, and the yeast plasmid was extracted according to the yeast plasmid extraction kit (purchased from Tiangen). The plasmids were electrotransformed into Top10 competent cells (purchased from Tiangen), coated on ampicillin-resistant plates, and cultured at 37° C. overnight. The monoclone was picked for sequencing to obtain the VHH gene sequence.

Example 2

Expression Vector Construction, Protein Expression and Purification of CAIX Nanobody The coding sequence of CAIX VHH antibody obtained by screening and the coding sequence of human IgG1 Fc segment were constructed into a fusion protein expression sequence by homologous recombination. Using the ExpiCHO™ Expression System kit (purchased from Thermo), the fusion protein expression plasmid prepared in a medium amount was transferred into Expi-CHO cells. The transfection method was in accordance with the commercial instructions. The supernatant was collected after the cells were cultured for 5 days, and the target protein was purified by sorting method with Protein A magnetic beads (purchased from GenScript), magnetic beads were resuspended with an appropriate volume (1-4 times the volume of magnetic beads) of binding buffer (PBS+0.1% Tween 20, pH 7.4), and added to the sample to be purified, and incubated at room temperature for 1 hour with gentle shaking during the period. The sample was placed on a magnetic stand (purchased from Beaver), the supernatant was discarded, and the magnetic beads were washed three times with binding buffer. Elution buffer (0.1M sodium citrate, pH 3.2) was added in a volume 3-5 times the volume of the magnetic beads, shaken at room temperature for 5-10 minutes, the sample was placed back on the magnetic stand, the eluted buffer was collected, transferred to a collection tube in which neutralization buffer (1M Tris, pH 8.54) had been added, and mixed well to complete the preparation.

Example 3

Detection of Protein-Level Affinity of CAIX Nanobody

ForteBio affinity assay was performed according to the existing method (Estep, P et al., High throughput solution based measurement of antibody-antigen affinity and epitope binning. MAbs, 2013.5(2):p. 270-8). Briefly, the sensor was equilibrated off-line in assay buffer for 30 min, then detected on-line for 60 s to establish a baseline, and the purified antibody obtained as described above was loaded onto the AHQ sensor on-line. The sensor was then placed in 100 nM PD-L1 antigen for 5 min, and then the sensor was transferred to PBS for dissociation for 5 min. Kinetic analysis was performed using a 1:1 binding model. The results were shown in Table 2.

TABLE 2

| Affinity of candidate molecules | | | |
|---|---|---|---|
| No. | KD (M) | Kon (1/Ms) | Koff (1/s) |
| H-YE-03 | 1.14E−09 | 1.24E+06 | 1.41E−03 |
| H-YE-04 | 2.82E−10 | 9.19E+05 | 2.59E−04 |

TABLE 2-continued

| | Affinity of candidate molecules | | |
|---|---|---|---|
| No. | KD (M) | Kon (1/Ms) | Koff (1/s) |
| H-YE-05 | 5.57E–10 | 1.19E+06 | 6.62E–04 |
| H-YE-23 | 2.18E–10 | 9.17E+05 | 2.00E–04 |
| H-YE-24 | 1.34E–09 | 5.94E+05 | 7.98E–04 |
| H-YE-25 | 1.21E–09 | 8.75E+05 | 1.06E–-03 |
| H-YE-26 | 1.09E–10 | 9.99E+05 | 1.09E–04 |
| H-YE-32 | 4.98E–10 | 9.88E+05 | 4.92E–04 |
| H-YE-33 | 2.04E–09 | 6.82E+05 | 1.39E–03 |
| H-YE-37 | 2.39E–09 | 1.04E+06 | 2.49E–03 |
| H-YE-38 | 5.29E–10 | 9.69E+05 | 5.13E–04 |
| H-YE-40 | 2.53E–09 | 4.95E+05 | 1.25E–03 |

Example 4

Detection of Cell-Level Affinity of CAIX Nanobody

CHO cells overexpressing human CAIX (CHO-hCAIX cells) were generated by the pCHO1.0 vector (purchased from Invitrogen) transfected with CAIX cDNA. The cell density of the proliferated CHO-CAIX cells were adjusted to $2 \times 10^6$ cells/ml, added at 100 μL/well to a 96-well flow cytometry plate, and centrifuged for later use. The purified CAIX antibody was diluted with PBS, and 3-fold dilution was started from 400 nM for a total of 12 points, and 100 μL/well of the above diluted sample was added to the above-mentioned 96-well flow cytometry plate with the cells, incubated at 4° C. for 30 min, and washed with PBS for two times. Goat F(ah')2 Anti-Human IgG-Fc(PE) (purchased from Abeam, ab98596) diluted 100 times with PBS was added at 100 μL/well, incubated at 4° C. for 30 min, and washed twice with PBS. PBS was added at 100 μl/well to resuspend the cells, the cells were detected on a CytoFlex (Bechman) flow cytometer, and the corresponding MFI was calculated.

In the experiment of the above method, the experimental results were shown in FIG. 1 and Table 3. All the purified samples of the present invention showed binding activity to CHO-hCAIX cells, and the binding activity values of some purified samples were higher than that of the single chain control antibody with a sequence derived from DANA Farber.

TABLE 3

| Binding capacity EC50 of CAIX nanobody to CHO-hCAIX at cell level | |
|---|---|
| No. | EC50 (nM) |
| DANA Farber | 5.468 |
| H-YE-03 | 7.344 |
| H-YE-04 | 7.78 |
| H-YE-05 | 8.795 |
| H-YE-23 | 3.549 |
| H-YE-24 | 3.055 |
| H-YE-25 | 2.442 |
| H-YE-26 | 4.457 |
| H-YE-32 | 6.145 |
| H-YE-33 | 2.779 |
| H-YE-37 | 6.066 |
| H-YE-40 | 4.743 |

Example 5

Detection of Protein-Level Affinity of CAIX-Humanized Nanobody

According to the characteristics of the sequence and affinity of the antibodies screened in the above examples, we selected 3 antibody strains H-YE-05, H-YE-23 and H-YE-32 to complete the sequence humanization transformation. The vector construction, expression and purification of the humanized antibody were completed with the humanized engineered sequence according to the method described in Example 2. Finally, two humanized recombinant antibodies were obtained from H-YE-05, named as Hu-H-YE-05-D3 and Hu-H-YE-05-D4; one humanized recombinant antibody was obtained from WYE-23, named as Hu-H-YE-23-D2; and two humanized antibodies were obtained from H-YE-32, named as Hu-H-YE-32-D6 and Hu-H-YE-32-D5. The purified humanized antibodies were subjected to protein-level affinity identification according to the method described in Example 3, and the results were shown in Table 4.

TABLE 4

| Detection results of protein-level affinity of CAIX humanized nanobody | | | |
|---|---|---|---|
| No. | KD (M) | Kon (l/Ms) | Koff (1/s) |
| H-YE-05 | 1.03E–08 | 1.55E+05 | 1.59E–03 |
| Hu-H-YE-05-D3 | 1.03E–08 | 1.79E+05 | 1.85E–03 |
| Hu-H-YE-05-D4 | 7.84E–09 | 1.81E+05 | 1.42E–03 |
| H-YE-23 | 4.08E–09 | 1.36E+05 | 5.56E–04 |
| Hu-H-YE-23-D2 | 6.68E–09 | 1.58E+05 | 1.05E–03 |
| H-YE-32 | 3.69E–10 | 2.71E+05 | 1.00E–04 |
| Hu-H-YE-32-D6 | 3.84E–10 | 2.60E+05 | 1.00E–04 |
| Hu-H-YE-32-D5 | 8.20E–09 | 2.16E+05 | 1.77E–03 |
| Gerentuximab | 1.01E–09 | 9.86E+04 | 1.00E–04 |

Example 6

Figure 2:
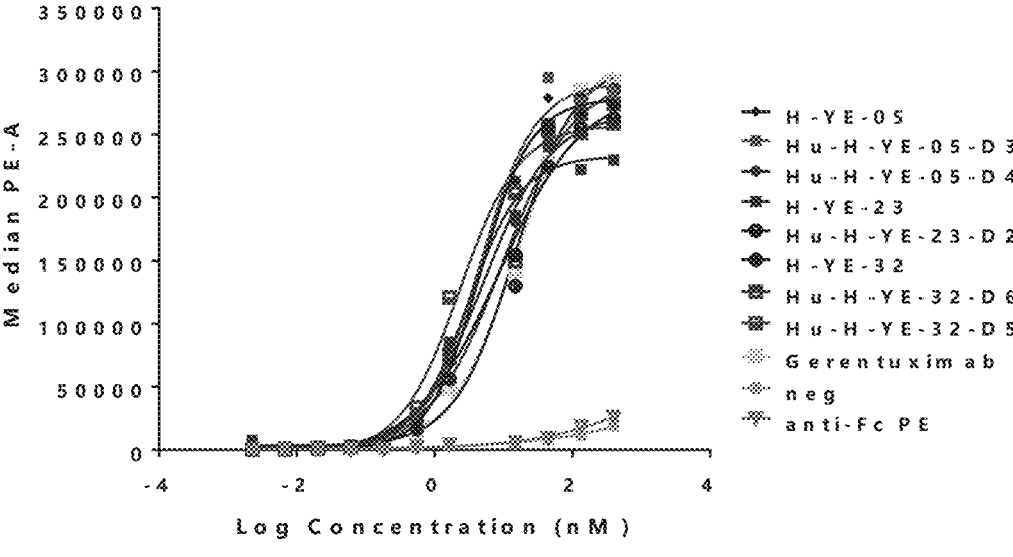
FIG. 2 shows the diagram of detection results of the affinity of humanized nanobodies to CHO-hCAIX at cell level.

Detection of Binding Capacity of CAM Humanized Nanobody to CHO-hCAIX at Cell Level and its Species Cross-Recognition Characteristics The purified humanized antibodies were subjected to the detection of binding capacity of the purified humanized nanobody to CHO-hCAIX at cell level according to the method described in Example 4, and the results were shown in FIG. 2 and Table 5.

TABLE 5

| Binding capacity EC50 between humanized nanobody and human CHO-hCAIX cell | |
|---|---|
| No. | EC50 (nM) |
| H-YE-05 | 4.549 |
| Hu-H-YE-05-D3 | 4.46 |
| Hu-H-YE-05-D4 | 5.065 |
| H-YE-23 | 3.107 |
| Hu-H-YE-23-D2 | 8.709 |
| H-YE-32 | 14.61 |
| Hu-H-YE-32-D6 | 9.611 |
| Hu-H-YE-32-D5 | 2.328 |
| Gerentuximab | 16.53 |

Figures 3, 4:
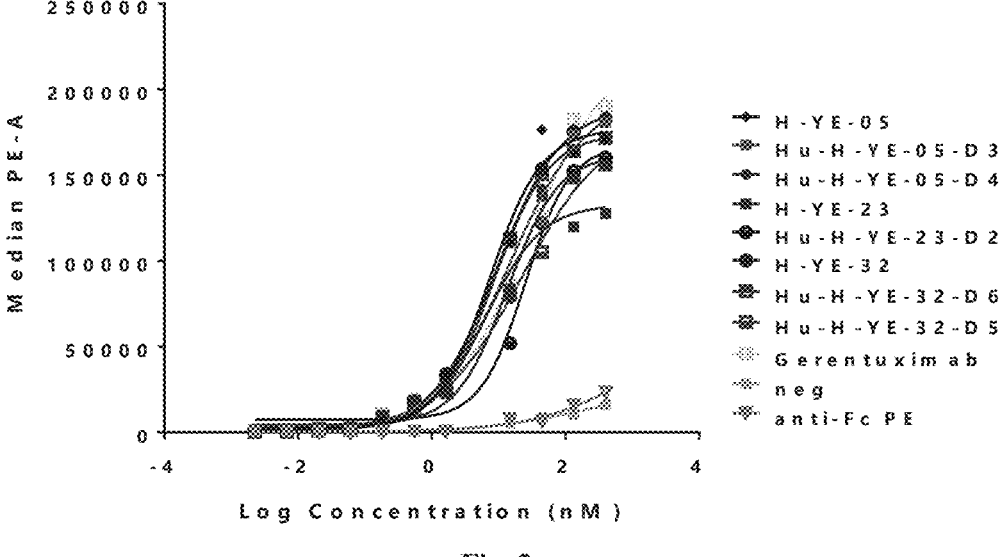
FIG. 3 shows the diagram of detection results of the affinity of humanized nanobodies to CHO-cyCAIX at cell level.
FIG. 4 shows the diagram of detection results of the affinity of humanized nanobodies to CHO-mCAIX at cell level.

In order to identify the affinity of the antibody to monkey CAIX (cyCAIX) at cell level, the cell strain was constructed according to the method described in Example 4, the affinity of the purified humanized antibody to CHO-cyCAIX was identified at cell level, and the results were shown in FIG. 3 and Table 6.

TABLE 6

Binding capacity EC50 of humanized
nanobody to monkey CHO-cyCAIX cell

| No. | EC50 (nM) |
| --- | --- |
| H-YE-05 | 7.323 |
| Hu-H-YE-05-D3 | 14.31 |
| Hu-H-YE-05-D4 | 13.46 |
| H-YE-23 | 6.552 |
| Hu-H-YE-23-D2 | 25.11 |
| H-YE-32 | 9.418 |
| Hu-H-YE-32-D6 | 8.393 |
| Hu-H-YE-32-D5 | 22.69 |
| Gerentuximab | 27.88 |

In order to identify the affinity of the antibody to murine CAIX (mCAIX) at cell level, the cell stain was constructed according to the method described in Example 4, the affinity of the purified humanized antibody to CHO-mCAIX at cell level was identified, and the results were shown in FIG. 4 and Table 7.

TABLE 7

Binding capacity EC50 of humanized
nanobody to mouse CHO-mCAIX cell

| No. | EC50 (nM) |
| --- | --- |
| H-YE-05 | 31.67 |
| Hu-H-YE-05-D3 | 20.82 |
| Hu-H-YE-05-D4 | 58.82 |
| H-YE-23 | 38.1 |
| Hu-H-YE-23-D2 | 43.69 |

TABLE 7-continued

Binding capacity EC50 of humanized
nanobody to mouse CHO-mCAIX cell

| No. | EC50 (nM) |
| --- | --- |
| H-YE-32 | 34.15 |
| Hu-H-YE-32-D6 | 59.65 |
| Hu-H-YE-32-D5 | 552.2 |
| Gerentuximab | 35.14 |

Discussion

Single-domain antibody (sdAb), also known as nanobody (nanobody) or heavy chain antibody (hcAb), is an antibody isolated from the serum of camelids and sharks, and its volume is about $\frac{1}{10}$ of that of traditional antibodies. Different from traditional antibodies, single-domain antibody is only composed of heavy chain, and its antigen-binding region is only a single-domain connected to the Fc region through a hinge region, and this antigen-binding region still has the ability of binding antigen after it is separated from the antibody. Single-domain antibody has the characteristics of small molecular weight and good stability. Compared with traditional common normal antibodies, they have good tissue infiltration, flexible administration methods, high degree of humanization, easy transformation to obtain recombinant proteins, and many other advantages in drug development and diagnostic reagent development.

All documents mentioned herein are incorporated by reference in the present application as if each document were individually incorporated by reference. In addition, it should be understood that after reading the above teaching content of the present invention, those skilled in the art can make various changes or modifications to the present invention, and these equivalent forms also fall within the scope defined by the appended claims of the present application.

Sequence Information of the Present Invention:

1. Amino acid (AA) sequences of CAIX-targeting nanobodies:

| Sequence No. | Clone No. | AA SEQ | CDR1 | CDR2 | CDR3 |
| --- | --- | --- | --- | --- | --- |
| 4 | H-YE-03 | QVQLQESGGGLVQPGGSLRLSCTASTSSFN FQTMGWYRQAPGKQRELVATITSRAITNY ADSVKGRFTISRDNAAKTVSLQMNSLKPE DTAVYYCNAAWIGDYWGQGTQVTVSA | TSSFNFQT | ITSRAIT | NAAWIGDY |
| 9 | H-YE-04 | QVQLQESGGGLVQPGGSLRLSCTASTSSFN FQTLGWYRQAPGNQRELVATITSRAITNYA DSVKGRFTISRDNAAKTVSLQMNSLKPED TAVYYCNAAWIGDYWGQGTQVTVSS | TSSFNFQT | ITSRAIT | NAAWIGDY |
| 14 | H-YE-05 | QVQLQESGGGLVOPGGSRRLSCAASGNSV NIFSFAAVAWYRQAPGKQRELVAVITTTGG TKYSDSVKGRFTISRDSAKNTVILQMNSL KPEDTAVYYCNADYLQDYWGQGTQVTVS S | GNSVNIFSF AA | ITTTGGT | NADYLQD Y |
| 19 | H-YE-23 | QVQLQESGGGLVQPGGSLRLSCAASGNSA NIFSFASVAWYRQAPGKQRELVAVITSAGG TKYSDSVKGRFTISRDNAKNTILLQMNSLK PEDTAVYYCNVDYLQDYWGQGTOVTVSS | GNSANIFSF AS | ITSAGGT | NVDYLQD |
| 24 | H-YE-24 | QVQLQESGGGLVQPGGSLRLSCAASGNSV NIFRFAAMAWYRQAPGKQRELVAVITSAG GTKYSDSVKGRFTISRDNAKNTVLLQMNS LKPEDTAVYYCNADYLQDYWGQGTQVTV SS | GNSVNIFRF AA | ITSAGGT | NADYLQD Y |

-continued

| Sequence No. | Clone No. | AA SEQ | CDR1 | CDR2 | CDR3 |
|---|---|---|---|---|---|
| 29 | H-YE-25 | QVQLQESGGGLVQPGGSLRLSCAASGNSV NIFRFAAMAWYRQAPGKQRELVAVITTTG GTKYSDSVKGRFTISRDSAKNTVLLQMNS LKPEDTAVYYCNADYLQDYWGQGTQVTV SS | GNSVNIFRF AA | ITTTGGT | NADYLQD Y |
| 34 | H-YE-26 | QVQLQESGGGLVQAGGSLRLSCAASGNSV NIFRFATVAWYRQAPGEQRELVAVITSAGG TKYSDSVKGRFTISRDNAKNTVLLQMNSL KPEDTAVYYCNADFLQDYWGQGTQVTVS S | GNSVNIFRF AT | ITSAGGT | NADFLQDY |
| 39 | H-YE-32 | QVQLQESGGGLVQPGGSLRLSCAASGGAR NIFSFAAMAWYRQAPGKQRELVAVITSAGG TQYSSSVKGRFTISRDNAKKTVLLQMNSL KPEDTAVYYCNADYYQDYWGQGTQVTVS S | GGARNIFSF AA | ITSAGGT | NADYYQD Y |
| 44 | H-YE-33 | QVQLQESGGGLVQPGGSLRLSCAASGGDF RFYDMGWYRQAPGKQRELVAGITTRGYT NYADVVKGRFTISRDNAKNTVYLEMNSLK PEDTAVYSCSASHFLGGRIDYWGQGTQVT VSS | GGDFRFYD | ITTRGYT | SASHFLGG RIDY |
| 49 | H-YE-37 | QVQLQESGGGLMHDGDSLRLSCAASGRTF STYAMGWFRQAPGKEREFVAAISWSGGST YYADSVKGRFTISRDNAKNTVYLQMNSLK PEDTAVYYCAAEGIYNSGSSYHDANGYDY WGQGTQVTVSS | GRTFSTYA | ISWSGGS T | AAEGIYNS GSSYHDAN GYDY |
| 54 | H-YE-38 | QVQLQESGGGLMQPGGSLTLSCAVPRFTL DYYAIGWFRQAPGKEREFVAAISWSGGTT QYSDSAKGRFTISRDNSKNTGYLQMNSLK PEDTATYYCAAGRQLEWRTYDYWGQGTQ VTVSS | RFTLDYYA | ISWSGGT T | AAGRQLE WRTYDY |
| 59 | H-YE-40 | QVQLQESGGGLVQAGGSLRLSCAASGRTF SSYAMGWFRQAPGKEREFVATISWNGGST YYADSVKGRFTISRDNAKNTVYLQMNSLK PEDTAVYYCAAEHDLGELAGTGYDYWGQ GTQVTVSS | GRTFSSYA | ISWNGGS T | AAEHDLGE LAGTGYDY |

40

2. DNA sequences of CAIX-targeting nanobodies:

| Sequence No. | Clone No. | DNA SEQ |
|---|---|---|
| 5 | H-YE-03 | CAGGTGCAGCTGCAGGAGTCTGGGGGAGGCTTGGTGCAGCCTGGGGGGTCTCT GAGACTCTCCTGTACAGCCTCTACTAGCAGTTTCAATTTCCAGACCATGGGCTG GTACCGCCAGGCTCCAGGGAAGCAGCGCGAGTTGGTCGCGACAATTACTAGCC GTGCTATCACAAACTATGCAGACTCCGTGAAGGGCCGCTTCACCATCTCCAGAG ACAACGCCGCGAAGACGGTGTCTCTGCAAATGAACAGCCTTAAACCTGAGGAC ACGGCCGTCTATTACTGTAATGCAGCGTGGATCGGGGACTACTGGGGCCAGGGG ACCCAGGTCACCGTCTCCGCA |
| 10 | H-YE-04 | CAGGTGCAGCTGCAGGAGTCTGGGGGAGGCTTGGTGCAGCCTGGGGGGTCTCT GAGACTCTCCTGTACAGCCTCTACTAGCAGTTTCAATTTCCAGACCTTGGGCTG GTACCGCCAGGCTCCAGGGAATCAGCGCGAGTTGGTCGCGACAATTACTAGCCG TGCTATCACAAACTATGCAGACTCCGTGAAGGGCCGCTTCACCATCTCCAGAGA CAACGCCGCGAAGACGGTGTCTCTGCAAATGAACAGCCTTAAACCTGAGGACA CGGCCGTCTATTACTGTAATGCAGCGTGGATCGGGGACTACTGGGGCCAGGGGA CCCAGGTCACCGTCTCCAGT |
| 15 | H-YE-05 | CAGGTGCAGCTGCAGGAGTCTGGGGGAGGCTTGGTGCAACCTGGGGGGTCTCG TCGACTCTCCTGTGCAGCCTCTGGAAACTCTGTAAACATCTTCAGTTTCGCTGCC GTGGCCTGGTACCGCCAGGCTCCAGGGAAGCAGCGCGAGTTGGTCGCAGTCAT TACTACGACAGGTGGCACTAAGTATTCAGACTCCGTGAAGGGCCGATTCACCAT CTCCAGAGACAGCGCCAAGAATACGGTGCTTCTGCAAATGAACAGCCTGAAAC CTGAGGACACGGCCGTCTATTACTGTAATGCAGATTATTTACAGGACTACTGGGG CCAGGGGACCCAGGTCACCGTCTCCAGT |

-continued

| Sequence No. | Clone No. | DNA SEQ |
|---|---|---|
| 20 | H-YE-23 | CAGGTGCAGCTGCAGGAGTCTGGAGGAGGCTTGGTGCAACCTGGGGGGTCTCT<br>AAGACTCTCCTGTGCAGCCTCTGGAAACTCTGCTAACATCTTCAGTTTCGCGTC<br>CGTGGCCTGGTACCGCCAGGCTCCAGGGAAACAGCGCGAGTTGGTCGCAGTGA<br>TCACTAGTGCAGGTGGCACTAAGTATTCAGACTCCGTGAAGGGCCGATTCACCA<br>TCTCCAGAGACAACGCCAAGAATACGATTCTTCTGCAAATGAACAGCCTGAAAC<br>CTGAGGACACGGCCGTCTATTACTGTAATGTAGATTATTTACAGGACTACTGGGG<br>CCAGGGGACCCAGGTCACCGTCTCCAGT |
| 25 | H-YE-24 | CAGGTGCAGCTGCAGGAGTCTGGGGGAGGCTTGGTGCAGCCTGGGGGGTCTCT<br>AAGACTCTCCTGTGCAGCCTCTGGAAACTCTGTAAACATCTTCAGATTCGCTGC<br>CATGGCCTGGTACCGCCAGGCTCCAGGGAAGCAGCGCGAGTTGGTCGCAGTCA<br>TTACTAGTGCAGGTGGCACTAAGTATTCAGACTCCGTGAAGGGCCGATTCACCA<br>TCTCCAGAGACAACGCCAAGAATACGGTGCTTCTGCAAATGAACAGCCTGAAA<br>CCTGAGGACACGGCCGTCTATTACTGTAATGCAGATTATTTACAGGACTACTGGG<br>GCCAGGGGACCCAGGTCACCGTCTCCAGT |
| 30 | H-YE-25 | CAGGTGCAGCTGCAGGAGTCTGGAGGAGGCTTGGTGCAACCTGGGGGGTCTCT<br>AAGACTCTCCTGTGCAGCCTCTGGAAACTCTGTAAACATCTTCAGATTCGCTGC<br>CATGGCCTGGTACCGCCAGGCTCCAGGGAAGCAGCGCGAGTTGGTCGCAGTCA<br>TTACTACGACAGGTGGCACTAAGTATTCAGACTCCGTGAAGGGCCGATTCACCA<br>TCTCCAGAGACAGCGCCAAGAATACGGTGCTTCTGCAAATGAACAGCCTGAAA<br>CCTGAGGACACGGCCGTCTATTACTGTAATGCAGATTATTTACAGGACTACTGGG<br>GCCAGGGGACCCAGGTCACCGTCTCCAGT |
| 35 | H-YE-26 | CAGGTGCAGCTGCAGGAGTCTGGGGGAGGCTTGGTGCAGGCTGGGGGGTCTCT<br>GAGACTCTCCTGTGCAGCCTCTGGAAACTCTGTGAACATCTTCAGGTTCGCTAC<br>CGTAGCCTGGTACCGCCAGGCTCCAGGGGAGCAGCGCGAGTTGGTCGCAGTCA<br>TTACTAGTGCAGGTGGCACTAAGTATTCAGACTCCGTGAAGGGCCGATTCACCA<br>TCTCCACAGACAACGCCAAGAATACGGTGCTTCTGCAAATGAACAGCCTGAAA<br>CCTGAGGACACGGCCGTCTATTATTGTAATGCAGATTTTTTACAGGACTACTGGG<br>GCCAGGGGACCCAGGTCACCGTCTCCAGT |
| 40 | H-YE-32 | CAGGTGCAGCTGCAGGAGTCTGGGGGAGGCTTGGTGCAACCTGGGGGGTCTCT<br>AAGACTCTCCTGTGCAGCCTCTGGAGGCGCTAGAAACATCTTCAGCTTCGCTGC<br>CATGGCCTCGTACCGCCAGGCTCCAGGGAAGCAGCGCGAGTTGGTCGCAGTCA<br>TTACTAGTGCAGGAGGCACGCAGTATTCAAGCTCCGTGAAGGGCCGATTCACCA<br>TCTCCAGAGACAACGCCAAGAAAACGGTATTGCTGCAAATGAACAGCCTGAAA<br>CCTGAGGACACGGCCGTCTATTACTGTAATGCAGATTATTATCAGGACTACTGGG<br>GCCAGGGGACCCAGGTCACCGTCTCCAGT |
| 45 | H-YE-33 | CAGGTGCAGCTGCAGGAGTCTGGAGGAGGCTTGGTGCAGCCTGGGGGGTCTCT<br>GAGACTCTCCTGTGCAGCCTCTGGAGGGGACTTCAGGTTCTATGACATGGGCTG<br>GTACCGCCAGGCTCCAGGGAAGCAGCGCGAGTTGGTCGCAGGTATTACTACTCG<br>TGGCTACACCAACTATGCAGACGTCGTGAAGGGCCGATTCACCATCTCCAGAGA<br>CAACGCCAAGAACACGGTGTATCTGGAAATGAACAGCCTGAAACCTGAGGACA<br>COGCCGTCTATTCCTGTAGTGCAAGTCACTTCCTGGGCGGGAGAATAGACTACT<br>GGGGCCAGGGGACCCAGGTCACCGTCTCCAGT |
| 50 | H-YE-37 | CAGGTGCAGCTGCAGGAGTCTGGAGGAGGATTGATGCATGATGGGGACTCTCT<br>GAGACTCTCCTGTGCAGCCTCTGGACGCACCTTCAGTACCTATGCCATGGGCTG<br>GTTCCGCCAGGCTCCAGGGAAGGAGCGTGAGTTTGTAGCAGCTATTAGCTGGA<br>GTGGTGGTAGCACATACTATGAGACTCCGTGAAGGGCCGATTCACCATCTCCA<br>GAGACAACGCCAAGAACACGGTGTATCTGCAAATGAACAGCCTGAAACCTGAG<br>GACACGGCCGTTTATTACTGTGCAGCAGAGGGGATATACAATAGTGGTAGTTCGT<br>ACCATGACGCGAACGGGTATGACTACTGGGGCCAGGGGACCCAGGTCACCGTC<br>TCCAGT |
| 55 | H-YE-38 | CAGGTGCAGCTGCAGGAGTCTGGGGGAGGCTTGATGCAGCCTGGGGGGTCTCT<br>GACGCTCTCCTGTGCAGTCCCTAGATTCACTTTGGATTATTATGCCATAGGCTGGT<br>TCCGGCAGGCCCCAGGGAAGGAGCGTGAATTTGTAGCAGCTATTAGCTGGAGT<br>GGTGGTACAACACAGTATTCAGACTCCGCGAAGGGCCGATTCACCATCTCCAGA<br>GACAACAGCAAGAATACGGGGTATCTGCAAATGAACAGCCTGAAACCTGAGGA<br>CACGGCGACTTATTACTGTGCAGCAGGTCGCCAACTGGAGTGGAGGACGTATGA<br>CTACTGGOGCCAGGGGACCCAGGTCACCGTCTCCAGT |
| 60 | H-YE-40 | CAGGTGCAGCTGCAGGAGTCTGGAGGAGGATTGGTGCAGGCTGGGGGGCTCTCT<br>GAGACTCTCCTGTGCAGCCTCTGGACGCACCTTCAGTAGCTATGCCATGGGCTG<br>GTTCCGCCAGGCTCCAGGGAAGGAGCGTGAGTTTGTAGCAACTATTAGCTGGAA<br>TGGTGGTAGCACATACTATGCAGACTCCGTGAAGGGCCGATTCACCATCTCCAG<br>AGACAACGCCAAGAACACGGTGrATCTGCAAATGAACAGCCTGAAACCTGAGG<br>ACACGGCCGTTTATTACTCTGCAGCAGAACATGATTTGGGGGAGCTGGCGGGAA<br>CTGGTTATGACTACTGGGGCCAGGGGACCCAGGTCACCGTCTCCAGT |

3. Amino acid (AA) sequences, nucleotide sequences (DNA) and sequence numbering of CDR1-3 of CAIX-targeting nanobodies

| Clone No. | CDR1 | CDR2 | CDR3 | Amino acid sequence | Nucleotide sequence |
|---|---|---|---|---|---|
| H-YE-03 | 1 | 2 | 3 | 4 | 5 |
| H-YE-04 | 6 | 7 | 8 | 9 | 10 |
| H-YE-05 | 11 | 12 | 13 | 14 | 15 |
| H-YE-23 | 16 | 17 | 18 | 19 | 20 |
| H-YE-24 | 21 | 22 | 23 | 24 | 25 |
| H-YE-25 | 26 | 27 | 28 | 29 | 30 |

-continued

| Clone No. | CDR1 | CDR2 | CDR3 | Amino acid sequence | Nucleotide sequence |
|---|---|---|---|---|---|
| H-YE-26 | 31 | 32 | 33 | 34 | 35 |
| H-YE-32 | 36 | 37 | 38 | 39 | 40 |
| H-YE-33 | 41 | 42 | 43 | 44 | 45 |
| H-YE-37 | 46 | 47 | 48 | 49 | 50 |
| H-YE-38 | 51 | 52 | 53 | 54 | 55 |
| H-YE-40 | 56 | 57 | 58 | 59 | 60 |

4. Amino acid sequences encoded by humanized CAIX nanobodies

| Sequence No. | Clone No. | AA SEQ | FR1 | FR2 | FR3 | FR4 |
|---|---|---|---|---|---|---|
| 61 | Hu-H-YE-05-D3 | EVQLLESGGGLVQPGGSLRLSCAASG NSVNIFSFAAMSWYRQAPGKGLELVA VITTTGGTKYSDSVKGRFTISRDNSK NTLYLQMNSLRAEDTAVYYCNADYL QDYWGQGTQVTVSS | EVQLLES GGGLVQP GGSLRLS CAAS | MSWYRQ APGKGLE LVAV | KYSDSVK GRFTISRD NSKNTLY LQMNSLR AEDTAVY YC | WGQGTQ VTVSS |
| 63 | Hu-H-YE-05-D4 | EVQLLESGGGLVQPGGSRRLSCAASG NSVNIFSFAAVAWYRQAPGKQRELVA VITTTGGTKYSDSVKGRFTISRDSSK NTVYLQMNSLRAEDTAVYYCNADYL QDYWGQGTQVTVSS | EVQLLES GGGLVQP GGSRRLS CAAS | VAWYRQ APGKQRE LVAV | KYSDSVK GRFTISRD SSKNTVY LQMNSLR AEDTAVY YC | WGQGTQ VTVSS |
| 65 | Hu-H-YE-23-D2 | QVQLVESGGGLVQPGGSLRLSCSASG NSANIFSFASVAWYRQAPGKGLELVS VITSAGGTKYSDSVKGRFTISRDNSK NTLYLQMNSLRAEDTAVYYCNVDYL QDYWGQGTLVTVSS | QVQLVES GGGLVQP GGSLRLS CSAS | VAWYRQ APGKGLE LVSV | KYSDSVK GRFTISRD NSKNTLY LQMNSLR AEDTAVY YC | WGQGTL VTVSS |
| 67 | Hu-H-YE-32-D6 | QVQLVESGGGLVQPGGSLRLSCSASG GARNIFSFAAMAWYRQAPGKGLELV AVITSAGGTQYSSSVKGRFTISRDNSK KTLYLQMNSLRAEDTAVYYCNADYY QDYWGQGTQVTVSS | QVQLVES GGGLVQP GGSLRLS CSAS | MAWYRQ APGKGLE LVAV | QYSSSVK GRFTISRD NSKKTLY LQMNSLR AEDTAVY YC | WGQGTQ VTVSS |
| 69 | Hu-H-YE-32-D5 | QVQLVESGGGLVQPGGSLRLSCSASG GARNIFSFAAMHWYRQAPGKGLELV AVITSAGGTYYADSVKGRFTISRDNS KKTLYLQMNSLRAEDTAVYYCNADY YQDYWGQGTQVTVSs | QVQLVES GGGLVQP GGSLRLS CSAS | MHWYRQ APGKGLE LVAV | YYADSVK GRFTISRD NSKKTLY LQMNSLR AEDTAVY YC | WGQGTQ VTVSS |

5. Nucleotide sequences encoding humanized CAIX nanobodies

| Sequence No. | Clone No. | DNA SEQ |
|---|---|---|
| 62 | Hu-H-YE-05-D3 | GAGGTGCAGCTGCTGGAGAGCGGCGGCGGCCTGGTGCAGCCCGGCGGCAG CCTGAGGCTGAGCTGCGCCGCCAGCGGCAACAGCGTGAACATCTTCAGCTT CGCCGCCATGAGCTGGTACAGGCAGGCCCCCGGCAAGGGCCTGGAGCTGGT GGCCGTGATCACCACCACCGGCGGCACCAAGTACAGCGACAGCGTGAAGGG CAGGTTCACCATCAGCAGGGACAACAGCAAGAACACCCTGTACCTGCAGAT GAACAGCCTGAGGGCCGAGGACACCGCCGTGTACTACTGCAACGCCGACTA CCTGCAGGACTACTGGGGCCAGGGCACCCAGGTGACCGTGAGCAGC |
| 64 | Hu-H-YE-05-D4 | GAGGTGCAGCTGCTGGAGAGCGGCGGCGGCCTGGTGCAGCCCGGCGGCAG CAGGAGGCTGAGCTGCGCCGCCAGCGGCAACAGCGTGAACATCTTCAGCTT CGCCGCCGTGGCCTGGTACAGGCAGGCCCCCGGCAAGCAGAGGGAGCTGGT GGCCGTGATCACCACCACCGGCGGCACCAAGTACAGCGACAGCGTGAAGGG CAGGTTCACCATCAGCAGGGACAGCAGCAAGAACACCGTGTACCTGCAGAT GAACAGCCTGAGGGCCGAGGACACCGCCGTGTACTACTGCAACGCCGACTA CCTGCAGGACTACTGGGGCCAGGGCACCCAGGTGACCGTGAGCAGC |

-continued

| Sequence No. | Clone No. | DNA SEQ |
|---|---|---|
| 66 | Hu-H-YE-23-D2 | CAGGTGCAGCTGGTGGAGAGCGGCGGCGGCCTGGTGCAGCCCGGCGGCAG CCTGAGGCTGAGCTGCAGCGCCAGCGGCAACAGCGCCAACATCTTCAGCTT CGCCAGCGTGGCCTGGTACAGGCAGGCCCCCGGCAAGGGCCTGGAGCTGGT GAGCGTGATCACCAGCGCCGGCGGCACCAAGTACAGCGACAGCGTGAAGG GCAGGTTCACCATCAGCAGGGACAACAGCAAGAACACCCTGTACCTGCAGA TGAACAGCCTGAGGGCCGAGGACACCGCCGTGTACTACTGCAACGTGGACT ACCTGCAGGACTACTGGGGCCAGGGCACCCTGGTGACCGTGAGCAGC |
| 68 | Hu-H-YE-32-D6 | CAGGTGCAGCTGGTGGAGAGCGGCGGCGGCCTGGTGCAGCCCGGCGGCAG CCTGAGGCTGAGCTGCAGCGCCAGCGGCGGCGCCCAGGAACATCTTCAGCTT CGCCGCCATGGCCTGGTACAGGCAGGCCCCCGGCAAGGGCCTGGAGCTGGT GGCCGTGATCACCAGCGCCGGCGGCACCCAGTACAGCAGCAGCGTGAAGGG CAGGTTCACCATCAGCAGGGACAACAGCAAGAAGACCCTGTACCTGCAGAT GAACAGCCTGAGGGCCGAGGACACCGCCGTGTACTACTGCAACGCCGACTA CTACCAGGACTACTGGGGCCAGGGCACCCAGGTGACCGTGAGCAGC |
| 70 | Hu-H-YE-32-D5 | CAGGTGCAGCTGGTGGAGAGCGGCGGCGGCCTGGTGCAGCCCGGCGGCAG CCTGAGGCTGAGCTGCAGCGCCAGCGGCGGCGCCAGGAACATCTTCAGCTT CGCCGCCATGCACTGGTACAGGCAGGCCCCCGGCAAGGGCCTGGAGCTGGT GGCCGTGATCACCAGCGCCGGCGGCACCTACTACGCCGACAGCGTGAAGGG CAGGTTCACCATCAGCAGGGACAACAGCAAGAAGACCCTGTACCTGCAGAT GAACAGCCTGAGGGCCGAGGACACCGCCGTGTACTACTGCAACGCCGACTA CTACCAGGACTACTGGGGCCAGGGCACCCAGGTGACCGTGAGCAGC |

25

6. Amino acid sequences of humanized CAIX nanobodies and sequence numbers of encoding nucleotide sequences

| Clone No. | AA SEQ | FR1 | FR2 | FR3 | FR4 | DNA SEQ |
|---|---|---|---|---|---|---|
| Hu-H-YE-05-D3 | 61 | 71 (corresponding to positions 1-25 of SEQ No. 61) | 72 (corresponding to positions 37-53 of SEQ No. 61) | 73 (corresponding to positions 61-98 of SEQ No. 61) | 74 (corresponding to positions 107-117 of SEQ No. 61) | 62 |
| Hu-H-YE-05-D4 | 63 | 75 (corresponding to positions 1-25 of SEQ No. 631 | 76 (corresponding to positions 37-53 of SEQ No.63) | 77 (corresponding to positions 61-98 of SEQ No.63) | 78 (corresponding to positions 107-117 of SEQ No.63) | 64 |
| Hu-H-YB-23-D2 | 65 | 79 (corresponding to positioiis 1-25 of SEQ No. 65) | 80 (corresponding to positions .37-5.3 of SEQ No. 65) | 81 (corresponding to positions 61-98 of SEQ No. 65) | 82 (corresponding to positions 107-117 of SEQ No. 65) | 66 |
| Hu-H-YE-32-D6 | 67 | 83 (corresponding to positions 1-25 of SEQ No. 67) | 84 (corresponding to positions 37-53 of SEQ No. 67) | 85 (corresponding to positions 61-98 of SEQ No. 67) | 86 (corresponding to positions 107-117 of SEQ No.67) | 68 |
| Hu-H-YB-32-D5 | 69 | 87 (corresponding to positions 1-25 of SEQ No. 69) | 88 (corresponding to positions 37-53 of SEQ No. 69) | 89 (corresponding to positions 61-98 of SEQ No. 69) | 90 (corresponding to positions 107-117 of SEQ No. 69) | 70 |

All documents mentioned herein are incorporated by reference in the present application as if each document were individually incorporated by reference. In addition, it should be understood that after reading the above teaching content of the present invention, those skilled in the art can make various changes or modifications to the present invention, and these equivalent forms also fall within the scope defined by the appended claims of the present application.

What is claimed is:

1. A complementarity determining region (CDR) of an anti-CAIX single-domain antibody VHH chain comprising:
    (1) CDR1 shown in SEQ ID NO. 11, CDR2 shown in SEQ ID NO. 12, and CDR3 shown in SEQ ID NO. 13;
    (2) CDR1 shown in SEQ ID NO. 16, CDR2 shown in SEQ ID NO. 17, and CDR3 shown in SEQ ID NO. 18;
    (3) CDR1 shown in SEQ ID NO. 36, CDR2 shown in SEQ ID NO. 37, and CDR3 shown in SEQ ID NO. 38;
    (4) CDR1 shown in SEQ ID NO. 1, CDR2 shown in SEQ ID NO. 2, and CDR3 shown in SEQ ID NO. 3;
    (5) CDR1 shown in SEQ ID NO. 6, CDR2 shown in SEQ ID NO. 7, and CDR3 shown in SEQ ID NO. 8;
    (6) CDR1 shown in SEQ ID NO. 21, CDR2 shown in SEQ ID NO. 22, and CDR3 shown in SEQ ID NO. 23;
    (7) CDR1 shown in SEQ ID NO. 26, CDR2 shown in SEQ ID NO. 27, and CDR3 shown in SEQ ID NO. 28; or
    (8) CDR1 shown in SEQ ID NO. 31, CDR2 shown in SEQ ID NO. 32, and CDR3 shown in SEQ ID NO. 33.

2. A VHH chain of an anti-CAIX single-domain antibody, the VHH chain comprises a framework region FR and the complementarity determining region CDR according to claim 1.

3. An anti-CAIX single-domain antibody, it is a single-domain antibody against a CAIX epitope, and has the VHH chain according to claim 2.

4. The anti-CAIX single-domain antibody according to claim 3, the single-domain antibody comprises one of the following:
    (i) a VHH chain having an amino acid sequence shown in SEQ ID NO. 14, 19, 39, 4, 9, 24, 29 or 34; or
    (ii) a VHH chain having an amino acid sequence shown in SEQ ID NO. 61, 63, 65, 67 or 69.

5. An immunoconjugate, wherein the immunoconjugate comprises:
    (a) the anti-CAIX single-domain antibody according to claim 3; and
    (b) a conjugation moiety selected from the group consisting of: a detectable label, a drug, a toxin, a cytokine, a radionuclide, an enzyme, a gold nanoparticle/nanorod, a nanomagnetic a particle, a viral coat protein or VLP, or combinations thereof.

6. An immunoconjugate, wherein the immunoconjugate comprises:
    (a) the VHH chain of the anti-CAIX single-domain antibody according to claim 2; and
    (b) a conjugation moiety selected from the group consisting of: a detectable label, a drug, a toxin, a cytokine, a radionuclide, an enzyme, a gold nanoparticle/nanorod, a nanomagnetic a particle, a viral coat protein or VLP, or combinations thereof.

7. A method for diagnosis or treatment of a CAIX-associated disease or condition, in a subject, the method comprising administering to a subject in need thereof an effective amount of the following:
    (a) the VHH chain of the anti-CAIX single-domain antibody according to claim 2; or
    (b) a CAIX antigen-targeting-related antibody-drug conjugate (ADC) comprising the VHH chain according to claim 2.

8. A polynucleotide, wherein the polynucleotide encodes a protein selected from the group consisting of:
    (a) the CDR region of the anti-CAIX single-domain antibody VHH chain according to claim 1;
    (b) a VHH chain of the anti-CAIX single-domain antibody comprising a framework region FR and the complementarity determining region CDR according to claim 1; or (c) an anti-CAIX single-domain antibody comprising a VHH chain which comprises a framework region FR and the complementarity determining region CDR according to claim 1.

9. An expression vector, wherein the expression vector comprises the polynucleotide according to claim 8.

10. A host cell, wherein the host cell comprises the expression vector according to claim 9.

11. A method for producing an anti-CAIX single-domain antibody, characterized in, comprising the steps of:

(a) culturing the host cell according to claim 10 under conditions suitable for the production of single-domain antibody, thereby obtaining a culture containing the anti-CAIX single-domain antibody; and (b) isolating or recovering the anti-CAIX single-domain antibody from the culture; and (c) optionally, purifying and/or modifying the CAIX single-domain antibody obtained in step (b).

12. A host cell, wherein its genome is integrated with the polynucleotide according to claim 8.

13. A method for producing an anti-CAIX single-domain antibody, characterized in, comprising the steps of:

(a) culturing the host cell according to claim 12 under conditions suitable for the production of single-domain antibody, thereby obtaining a culture containing the anti-CAIX single-domain antibody; and (b) isolating or recovering the anti-CAIX single-domain antibody from the culture; and (c) optionally, purifying and/or modifying the CAIX single-domain antibody obtained in step (b).

\* \* \* \* \*